US008738106B2

(12) United States Patent  (10) Patent No.: US 8,738,106 B2
Rabinowitz et al.  (45) Date of Patent: May 27, 2014

(54) DEVICE, SYSTEM AND METHOD FOR IN VIVO ANALYSIS

(75) Inventors: Elisha Rabinowitz, Haifa (IL); Emil-Israel Katz, Savyon (IL)

(73) Assignee: Given Imaging, Ltd, Yoqneam (IL)

( * ) Notice: Subject to any disclaimer, the term of this patent is extended or adjusted under 35 U.S.C. 154(b) by 1683 days.

(21) Appl. No.: 11/831,857

(22) Filed: Jul. 31, 2007

(65) Prior Publication Data

US 2008/0146896 A1 Jun. 19, 2008

Related U.S. Application Data

(63) Continuation-in-part of application No. PCT/IL2007/000458, filed on Apr. 10, 2007, and a continuation-in-part of application No. PCT/IL2006/000127, filed on Jan. 31, 2006.

(60) Provisional application No. 60/647,790, filed on Jan. 31, 2005, provisional application No. 60/788,114, filed on Apr. 3, 2006.

(51) Int. Cl.
*A61B 5/1455* (2006.01)

(52) U.S. Cl.
USPC .......................... 600/310; 600/317; 600/302

(58) Field of Classification Search
USPC ......... 600/310, 322, 342, 473, 476, 104, 109, 600/160; 422/82.05, 82.06, 82.07, 82.08, 422/82.09, 82.11; 356/300
See application file for complete search history.

(56) References Cited

U.S. PATENT DOCUMENTS

| | | | |
|---|---|---|---|
| 3,971,362 A | 7/1976 | Pope et al. | |
| 4,017,261 A | 4/1977 | Svoboda et al. | |
| 4,038,485 A | 7/1977 | Johnston et al. | |
| 4,239,040 A | 12/1980 | Hosoya et al. | |
| 4,278,077 A | 7/1981 | Mizumoto | |
| 4,337,222 A | 6/1982 | Kitajima et al. | |
| 4,439,197 A | 3/1984 | Honda et al. | |
| 4,605,630 A | 8/1986 | Kung et al. | |

(Continued)

FOREIGN PATENT DOCUMENTS

| | | |
|---|---|---|
| DE | 34 40 177 | 5/1986 |
| EP | 1 002 229 | 1/2004 |

(Continued)

OTHER PUBLICATIONS

Office Action, issued Dec. 9, 2011, for U.S. Appl. No. 11/883,351.

(Continued)

*Primary Examiner* — Eric Winakur

(74) *Attorney, Agent, or Firm* — Pearl Cohen Zedek Latzer Baratz LLP

(57) ABSTRACT

A device for in vivo analysis includes: a reaction chamber to store a detecting reagent able to react with a sample collected in vivo; and optionally a labeled-substance chamber to store a labeled substance able to bind to at least a portion of a compound resulting from a reaction of the detecting reagent and the sample. The in-vivo imaging device, typically an autonomous capsule, may have a housing, the housing comprising a window; an illumination source located within the housing to illuminate a body lumen through the window; an imager to receive light reflected from the body lumen through the window; and a transmitter to transmit image data to a receiving system. The window is coated with liposomes containing a marker such that the imager may acquire images which include the marking.

22 Claims, 13 Drawing Sheets

(56) References Cited

U.S. PATENT DOCUMENTS

| | | |
|---|---|---|
| 4,689,621 A | 8/1987 | Kleinberg |
| 4,803,992 A | 2/1989 | Lemelson |
| 4,844,076 A | 7/1989 | Lesho et al. |
| 4,885,077 A | 12/1989 | Karakelle et al. |
| 4,920,045 A | 4/1990 | Okuda et al. |
| 5,042,486 A | 8/1991 | Pfeiler et al. |
| 5,081,040 A | 1/1992 | Patel et al. |
| 5,109,870 A | 5/1992 | Silny et al. |
| 5,114,864 A | 5/1992 | Walt |
| 5,211,165 A | 5/1993 | Dumoulin et al. |
| 5,252,494 A | 10/1993 | Walt |
| 5,279,607 A | 1/1994 | Schentag et al. |
| 5,306,623 A | 4/1994 | Kiser et al. |
| 5,330,427 A | 7/1994 | Weissenburger |
| 5,362,478 A | 11/1994 | Desai et al. |
| 5,385,846 A | 1/1995 | Kuhn et al. |
| 5,395,366 A | 3/1995 | D'Andrea et al. |
| 5,429,132 A | 7/1995 | Guy et al. |
| 5,443,701 A | 8/1995 | Willner et al. |
| 5,447,868 A | 9/1995 | Augurt |
| 5,460,969 A | 10/1995 | Fielder et al. |
| 5,479,935 A | 1/1996 | Essen-Moller |
| 5,490,969 A | 2/1996 | Bewlay et al. |
| 5,558,640 A | 9/1996 | Pfeiler et al. |
| 5,563,071 A | 10/1996 | Augurt |
| 5,604,531 A | 2/1997 | Iddan et al. |
| 5,762,770 A | 6/1998 | Pritchard et al. |
| 5,800,350 A | 9/1998 | Coppleson et al. |
| 5,814,525 A | 9/1998 | Renschler et al. |
| 5,819,736 A | 10/1998 | Avny et al. |
| 5,833,602 A | 11/1998 | Osemwota |
| 5,833,603 A | 11/1998 | Kovacs et al. |
| 5,837,196 A | 11/1998 | Pinkel et al. |
| 5,853,005 A | 12/1998 | Scanlon |
| 5,892,144 A | 4/1999 | Meller et al. |
| 5,913,820 A | 6/1999 | Bladen et al. |
| 5,916,176 A | 6/1999 | Caillouette |
| 5,919,633 A | 7/1999 | Tausk et al. |
| 5,932,480 A | 8/1999 | Maruo et al. |
| 5,968,765 A | 10/1999 | Grage et al. |
| 5,993,378 A | 11/1999 | Lemelson |
| 6,043,080 A | 3/2000 | Lipshutz et al. |
| 6,080,423 A | 6/2000 | Charych et al. |
| 6,099,482 A | 8/2000 | Brune et al. |
| 6,149,581 A | 11/2000 | Klingenstein |
| 6,162,469 A | 12/2000 | Atarashi et al. |
| 6,240,312 B1 | 5/2001 | Alfano et al. |
| 6,285,897 B1 | 9/2001 | Kilcoyne et al. |
| 6,330,464 B1 | 12/2001 | Colvin, Jr. et al. |
| 6,369,812 B1 | 4/2002 | Iyriboz et al. |
| 6,395,562 B1 | 5/2002 | Hammock et al. |
| 6,453,928 B1 | 9/2002 | Kaplan |
| 6,475,145 B1 | 11/2002 | Baylor |
| 6,488,694 B1 | 12/2002 | Lau et al. |
| 6,766,817 B2 | 7/2004 | Dias Da Silva |
| 6,918,404 B2 | 7/2005 | Dias Da Silva |
| 7,066,586 B2 | 6/2006 | Dias Da Silva |
| 7,201,872 B2 | 4/2007 | Meron |
| 7,684,840 B2 | 3/2010 | Palti |
| 2001/0035902 A1 | 11/2001 | Iddan et al. |
| 2002/0001695 A1 | 1/2002 | Tajima et al. |
| 2002/0015952 A1 | 2/2002 | Anderson et al. |
| 2002/0042562 A1 | 4/2002 | Meron et al. |
| 2002/0103417 A1 | 8/2002 | Gazdzinski |
| 2002/0109774 A1 | 8/2002 | Meron et al. |
| 2002/0111544 A1 | 8/2002 | Iddan et al. |
| 2002/0146368 A1 | 10/2002 | Meron et al. |
| 2002/0173718 A1 | 11/2002 | Frisch et al. |
| 2002/0177779 A1 | 11/2002 | Adler et al. |
| 2002/0198439 A1 | 12/2002 | Mizuno |
| 2003/0020810 A1 | 1/2003 | Takizawa et al. |
| 2003/0023150 A1 | 1/2003 | Yokoi et al. |
| 2004/0115877 A1 | 6/2004 | Iddan |
| 2004/0126421 A1 | 7/2004 | Turk |
| 2005/0075555 A1 | 4/2005 | Glukhovsky et al. |
| 2005/0131287 A1 | 6/2005 | Kaylor et al. |
| 2008/0114225 A1 | 5/2008 | Rabinovitz |
| 2008/0146896 A1 | 6/2008 | Rabinovitz |
| 2009/0318766 A1 | 12/2009 | Rabinovitz |
| 2010/0322866 A1 | 12/2010 | Rabinovitz |

FOREIGN PATENT DOCUMENTS

| | | |
|---|---|---|
| FR | 2 688 997 | 10/1993 |
| JP | 52-094681 | 8/1977 |
| JP | 57-163309 | 10/1982 |
| JP | 62-240038 | 10/1987 |
| JP | 4109927 | 4/1992 |
| JP | 4138128 | 5/1992 |
| JP | 5015515 | 1/1993 |
| JP | 5200015 | 8/1993 |
| JP | 6285044 | 10/1994 |
| JP | 7111985 | 5/1995 |
| JP | 11-509094 | 8/1999 |
| JP | 2002-010990 | 12/2001 |
| JP | 2004/523274 | 8/2004 |
| JP | 2004/529733 | 9/2004 |
| JP | 2004-350512 | 12/2004 |
| RU | 2191569 | 10/2002 |
| WO | WO 96/23524 | 8/1996 |
| WO | WO 97/02357 | 1/1997 |
| WO | WO 97/45720 | 12/1997 |
| WO | WO 98/07366 | 2/1998 |
| WO | WO 99/11754 | 3/1999 |
| WO | WO 99/32028 | 7/1999 |
| WO | WO 00/22975 | 4/2000 |
| WO | WO 01/08548 | 2/2001 |
| WO | WO 01/53792 | 7/2001 |
| WO | WO 02/055984 | 7/2002 |
| WO | WO 02/102243 | 12/2002 |
| WO | WO 2004/014227 | 2/2004 |
| WO | WO 2004/103351 | 12/2004 |
| WO | WO 2004/105946 | 12/2004 |
| WO | WO 2005/003723 | 1/2005 |
| WO | WO 2005/084534 | 9/2005 |
| WO | WO 2005/113374 | 12/2005 |

OTHER PUBLICATIONS

Office Action, issued Nov. 17, 2011, for U.S. Appl. No. 12/294,679.
Supplementary European Search Report for European Patent Application No. 06 70 1723.6, mailed Dec. 23, 2009.
International Search Report, issued Dec. 4, 2006, for International Patent Application No. PCT/IL2006/00127.
Supplemental European Search Report for European Patent Application No. 07 73 6198.8, mailed on Mar. 1, 2010.
International Search Report for International Application No. PCT/IL06/00127, Oct. 30, 2006.
U.S. Appl. No. 12/294,679 mailed Mar. 6, 2012.
U.S. Appl. No. 12/294,679 mailed Jun. 27, 2012.
Final Office Action for U.S. Appl. No. 12/294,679 mailed Oct. 11, 2012.
Office Action for U.S. Appl. No. 12/294,656 mailed Apr. 10, 2012.
Final Office Action for U.S. Appl. No. 12/294,656 mailed Aug. 16, 2012.
Video Camera to "TAKE"—RF System Lab, Dec. 25, 2001.
"New Smart Plastic has Good Memory"—Turke, European Medical Device Manufacturer, devicelink.com.
The Radio Pill, Rowlands, et al., British Communications and Electronics, Aug. 1960, pp. 598-601.
Wellesley company sends body montiors into space—Crum, Apr. 1998.
Wireless transmission of a color television moving image from the stomach using a miniature CCD camera, light source and microwave transmitter. Swain CP, Gong F, Mills TN. Gastrointest Endosc 1997;45:AB40.
In vitro leucocyte adhesion to modified polyurethane surfaces—Bruil, Biomaterials 1992, vol. 13, No. 13.
Medical Diagnosis Reagents, vol. 16.
Heidelberger Kapsel—ein Kleinstsender fur die pH-Messung im Magen, Lange, et al., Telefunken-Zeitung, Jg 36 (1963) Heft 5, pp. 265-270.

DEVICE, SYSTEM AND METHOD FOR IN VIVO ANALYSIS

CROSS-REFERENCE TO RELATED APPLICATIONS

This application is a Continuation-in-Part under 35 U.S.C. §120 of PCT International Application No. PCT/IL2006/000127, International Filing Date Jan. 31, 2006, which claimed priority from U.S. Patent Application No. 60/647,790, filed Jan. 31, 2005. This application is also a Continuation-in-Part under 35 U.S.C. §120 of PCT International Application No. PCT/IL2007/000458, International Filing Date Apr. 10, 2007, which claimed priority from U.S. Patent Application No. 60/788,114, filed Apr. 3, 2006 which is hereby incorporated by reference.

FIELD OF THE INVENTION

The present invention relates in general to in vivo analysis, and specifically to in vivo analysis utilizing micro-fluidic techniques of body fluids possibly on a solid state substrate and utilizing liposomes and/or nano-containers.

BACKGROUND OF THE INVENTION

An atypical concentration or presence of substances in body fluids or in body lumens may be indicative of the biological condition of the body. For example, the presence of elevated concentrations of red blood cells in the gastrointestinal (GI) tract may indicate different pathologies, depending on the location of the bleeding along the GI tract. Early detection, identification and location of abnormal conditions may be critical for correctly diagnosing and treating various pathologies.

In some cases diseases, such as, for example, cancer may be detected by analyzing the blood stream for tumor specific markers, for example, specific antibodies. One of the drawbacks of this method is that the appearance of antibodies in the blood stream may usually occur at a late stage of the disease, such that early detection may not be possible.

Detection of some pathologies in the GI tract may be performed using an endoscope; however, such detection may be limited to the upper or lower gastrointestinal tract. Thus, pathologies in other parts of the GI tract, such as, for example, the small intestine, may not be easily detected by endoscopy.

In vitro testing of body fluid samples for the presence of a suspected substance may be performed. For example, immunoassays may be used for the determination, either qualitative or quantitative, of some substances, such as, for example, peptides, proteins, enzymes, hormones, vitamins, drugs, carbohydrates, or the like, in a sample. In a typical immunoassay, to detect the presence, or measure the concentration, of an analyte or marker of interest, especially in a liquid sample, the analyte has to be separated from the test of the proteins in the sample. This is typically performed by specifically binding the analyte to a binding component for the analyte, followed by a separation process that extracts the bonded species from the rest of the sample. As the bonding reaction might be slow, the sample and the binding component for the marker (analyte) are usually incubated for a sufficient time to allow a market contained in the sample to bind to the binding component. A typical example of such a binding component may be a marker-specific antibody, e.g., a monoclonal antibody with specificity for the marker in question. However, other kinds of substances and structures may also qualify as a binding component.

Typically these in vitro methods of detection are carried out in a lab using cumbersome and complicated machines. Complicated machines may be needed, for example, because of the complicated requirements of such procedures which may involve multiple reactions and/or different conditions for each reaction, and typically washing in between reactions. Furthermore, these methods of detection, when carried out in vitro, may not easily enable the localization or identification of the origin of an abnormally occurring substance.

In many instances, locating an abnormally occurring substance in a body lumen may greatly contribute to the identification of pathology, and thus may contribute to the facile treatment of the identified pathology.

SUMMARY OF THE INVENTION

Some embodiments of the invention may allow, for example, analysis of a sample, such as, for example, a body fluid sample, typically by using a self contained, possibly single use, detection system.

According to some embodiments of the invention, a detection system may transport a fluid sample to a reaction chamber, or may transport samples, buffers or reactants, for example, from a storage compartment to a reaction chamber or compartment.

According to some embodiments of the invention, a detection system may include, for example, a means for detecting optical or other changes within the system. A detection system may include, for example, one or more detection units.

According to some embodiments of the invention, a detection unit may include two or more chambers or compartments fluidically connected, which may have a barrier or gate there between, the gate may be able to time and/or control fluid passage from one compartment to another.

According to some embodiments of the invention, a chamber, such as, for example, a storage chamber, may be connected to a second chamber, such as, for example, a waste chamber, via a passage, e.g., a tube having a typically controllable gate. Fluid may be transferred from a storage chamber to a waste chamber, e.g., when the gate is opened. The waste chamber may include, for example, an absorbent material, e.g., for receiving and holding fluids transferred to the waste chamber. In some embodiments, for example, a pressure gradient within the detection unit may cause a fluid sample or a body of fluid to be displaced, e.g. to another chamber.

Some embodiments of the invention may include, for example, sampling and fluidics methods which may involve having pressure gradients within a detection unit or system. Typically, movement of a body of fluid within a detection system or unit is in one direction, for example, towards a waste chamber.

Some embodiments of the invention may be implemented, for example, with solid state supports, and/or may utilize micro-fluidic technology. Some embodiments may be implemented on other supports, such as, for example, plastic or glass supports. Some embodiments may be designed or configured for use in a human body, i.e., in vivo, whereas other embodiments may be designed or configured for ex vivo or in vitro use.

A kit according to some embodiments of the invention may be used as a "point of care", allowing a care giver to perform analysis of body samples or other samples on the spot and obtain results, for example, obviating a need to use services of a special laboratory. Substantially automated analysis may be preformed according to some embodiments of the invention.

According to some embodiments, an in vivo device, e.g., an ingestible capsule (e.g., an autonomous in vivo device), having a sampling and analyzing or detecting system may be inserted (e.g., by swallowing) into a person's body lumen, for example, the gastrointestinal (GI) tact. Samples from the body lumen may be collected and analyzed on board, while the in vivo capsule is in the person's body.

According to some embodiments, the ingestible device may include an imaging device. In one example, a sampling point may be imaged by an imager of the imaging device, and image data from the imager may be transmitted and displayed outside the person's body, possibly together with other analysis results.

According to some embodiments, other detection methods may be employed, and data other than image data may be transmitted from the persons' body.

In some embodiments, for example, an ingestible device may include a reaction chamber to store a detecting reagent able to react with a sample collected in vivo; a sampling chamber to store the sample collected in vivo; a tube to transfer the sample from the sampling chamber to the reaction chamber; and a gate to allow passage of the sample in the tube.

In some embodiments, for example, the detecting reagent may be unlabeled; the sampling chamber may include a dry buffer; the detecting reagent may include an antibody; and the detecting reagent may be immobilized in the reaction chamber.

In some embodiments, for example, the ingestible device may further include a labeled-substance chamber to store a labeled substance able to bind to at least a portion of a compound resulting from a reaction of the detecting reagent and the sample. The labeled substance may include, for example, a conjugated dry antibody and/or a conjugated antibody in liquid buffet. The antibodies may be conjugated to optically detectable particles, e.g. gold particles, colored polymer particles, particles with fluorescence properties, colored particles or liposomes.

In some embodiments, for example, the detection system may further include a waste chamber to store an excess of the sample. In some embodiments, for example, the waste chamber may be vacuum-packed. In some embodiments, for example, the waste chamber may include an absorbent to absorb the excess of the sample and/or to drive the liquid in the diagnostic device.

In some embodiments, for example, the detection system device may further include a washing mechanism to wash the reaction chambers.

In some embodiments, for example, the gate may include a pH-sensitive gate and/or a temperature-sensitive gate.

In some embodiments, for example, the detection system may further include a mixing element, e.g., a piezoelectric element, to facilitate mixing of the sample and the detecting reagent.

In some embodiments, for example, the ingestible device may further include an in vivo sensor to sense at least a portion of the binding result.

In some embodiments, for example, the ingestible device may further include an in vivo imager to acquire an image of at least a portion of the binding result.

In some embodiments, for example, the ingestible device may be autonomous.

In some embodiments, for example, the ingestible device may include a swallowable capsule.

In some embodiments, for example the ingestible device may include a transmitter to transmit the image data to an external receiver and monitor.

In some embodiments, for example, the ingestible, in-vivo imaging device may be coated with liposomes or nano-containers containing a marker, an indicator, a signaling agent or a signaling material. The liposomes or nano-containers may react to a certain antigen in-vivo; following the reaction of the liposomes or nano-containers with the antigen, the signaling material may become visible, may become detectable, and/or may modify its optical property. The in-vivo imaging device may acquire images including the signaling material, thereby indicating the in-vivo presence of the antigen that reacts with the liposomes or nano-containers used.

In some embodiments, for example, a method may include: collecting a liquid sample in vivo; reacting in vivo the collected sample with a detecting reagent; binding a labeled substance to at least a portion of a compound resulting from a reaction of the detecting reagent and the sample; and sensing or imaging at least a portion of the binding result.

Embodiments of the invention may provide additional and/or other benefits and/or advantages.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be under stood by reference to the following detailed description when read with the accompanying drawings in which:

Figure 1:
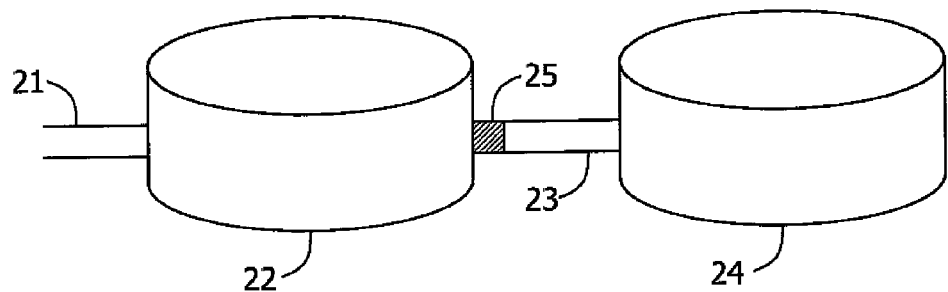
FIG. 1 is a schematic illustration of a detection unit according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Some embodiments of the present invention are directed to a typically one time use or partially single use detecting device, which may be used as an in vitro analysis kit. Other embodiments of the present invention are directed to a typically in vivo device, e.g. a swallowable device that may passively or actively progress through the gastro-intestinal (GI) tract, pushed along, in some embodiments, by natural peristalsis. Some embodiments are directed to in vivo sensing devices that may be passed through other body lumens such as, for example, through blood vessels, the reproductive tract, etc. The in vivo device may be, for example, a sensing device, an imaging device, a diagnostic device, a therapeutic device, or a combination thereof. In some embodiments, the in vivo device may include an image sensor or an imager. Other sensors may be included, for example, a pH sensor, a temperature sensor, and a pressure sensor, sensors of other in vivo parameters or compounds, or the like.

Devices and methods, including in vivo sensing devices, receiving systems, and display systems, according to embodiments of the present invention may be similar to embodiments described in U.S. Pat. No. 5,604,531 to Iddan et al., entitled "In Vivo Video Camera System", and/or in U.S. patent application Ser. No. 09/800,470, entitled "A Device and System for. In vivo Imaging", filed on Mar. 8, 2001, published on Nov. 1, 2001 as United States Patent Application Publication Number 2001/0035902, and/or in U.S. patent application Ser. No. 10/046,541, entitled "System and Method for Wide Field Imaging of Body Lumens", filed on Jan. 16, 2002, published on Aug. 15, 2002 as United States Patent Application Publication Number 2002/0109774, and/or in U.S. patent application Ser. No. 10/046,540, entitled "System and Method for Determining In Vivo Body Lumen Conditions", filed on Jan. 16, 2002, published on Aug. 15, 2002 as United States Patent Application Publication Number 2002/0111544, all of which are hereby incorporated by reference in their entirety. Devices as described herein may have other configurations and sets of components. An external receiver/recorder unit, a processor and a monitor, e.g., in a workstation, such as those described in the above publications, may be suitable for use with some embodiments of the present invention. Devices and systems as described herein may have other configurations and/or other sets of components. For example, the present invention may be practiced using an endoscope, needle, stent catheter, etc. Some in vivo devices may be capsule shaped, or may have other shapes, for example, a peanut shape or tubular, spherical, conical, or other suitable shapes.

Some embodiments of the present invention may include, for example, a typically swallowable in vivo device. In other embodiments, an in vivo device need not be swallowable and/or autonomous, and may have other shapes or configurations. Some embodiments may be used in various body lumens, for example, the GI tract, blood vessels, the urinary tract, the reproductive tract, or the like. In some embodiments, the in vivo device may optionally include a sensor, an imager, and/or other suitable components.

Embodiments of the in vivo device are typically autonomous and are typically self-contained. For example, the in vivo device may be or may include a capsule. Or other unit where all the components are substantially contained within a container, housing or shell, and where the in vivo device does not require any wires or cables to, for example, receive power or transmit information. The in vivo device may communicate with an external receiving and display system to provide display of data, control, or other functions. For example, power may be provided by an internal battery or a wireless receiving system. Other embodiments may have other configurations and capabilities for example, components may be distributed over multiple sites or units. Control information may be received from an external source.

FIG. 1 is a schematic illustration of a detection unit and/or a basic module of a detection system according to an embodiment of the invention. In some embodiments, an analyzing or detecting unit 200 may include, for example, an inlet 21, a reaction chamber 22, a waste chamber 24 and a gate 25 to control, for example, the passage from the reaction chamber to the waste chamber and from the inlet 21 to the reaction chamber 22. The reaction chamber 22 and the waste chamber 24 may be connected, for example, by a tube 23 plugged by gate 25. Although the example shown in FIG. 1 illustrates a reaction chamber 22 and waste chamber 24, other chambers, such as, for example, storage chambers may be included in unit 200. The tube 23 may be, for example, a capillary or any other suitable connecting passage. Gate 25 may be activated by a change in temperature (e.g. wax that melts when the device teaches a specified temperature, e.g. body temperature), by electrical command, or by other controllable methods. According to some embodiments, one or more chambers in unit 200 may be a storage chamber and may include, for example, buffers and/or reagents. Gate 25 may be similar to gating mechanisms that may be described in International Patent Application Number PCT/IL2005/000524 entitled "Device, System and Method for In-Vivo Sampling", and published under International Publication Number WO2005/113374 on Dec. 1, 2005 which is hereby incorporated by reference in its entirety.

According to some embodiments, one or more types of reactions may occur in reaction chamber 22. For example, a molecule capable of changing optical properties of a substrate, e.g., TMB (tetra-methyl benzidine) may be attached to a target analyte. An antibody, or other binding molecule for the target analyte, may be immobilized to reaction chamber 22, such that the target analyte will adhere to the antibody and the molecule attached to it will essentially be immobilized to the reaction chamber 22 when the molecule-analyte containing sample passes through the reaction chamber 22. The gathering of the molecule in reaction chamber 22 may cause, for example, an optical change in reaction chamber 22.

It should be appreciated that the term "antibody" as used throughout the specification and claims may include a complete polypeptide or functional parts of the polypeptide such as antigen binding fragments (Fab) that include the variable ends of an antibody or any analogs (including synthetic peptides) with a similar functionality.

In one embodiment, the reaction chamber 22 may contain, for example, immobilized nanocontainers for carrying imaging agents that may be specifically reactant to a target analyte. Known nanocontainers may include, for example, liposomes, colloidosomes and/or polymerosomes. Other known nonocontainers may be used. According to one embodiment of the present invention, liposomes may include bilayers of phospholipids around a hydrophobic core. In another embodiment, the liposome may be composed of more than bilayer and may consist of a multilayer of confronting lipid layers.

According to one embodiment of the present invention, conjugated nanocontainers, e.g. liposomes, may be filled with, for example, pH sensitive color in low strength buffer possessing a pH different from and/or opposite that of the sample and/or analyte. Rupture of the nanocontainers may occur as a result of a reaction with a target analyte. Upon rupturing of the nanoparticles and exposure of, for example, the pH sensitive color to the sample, a change of color may occur that may be, for example, optically detectable and/or visible. In other examples, the nanocontainers, e.g. the polymersome, may be filled with an alternate or additional molecule (e.g. fluorescence material, material having fluorescence properties) capable of changing optical properties of a substrate.

According to one embodiment, the nanoparticles with anti-targeting agents (e.g. antibodies) may be immobilized to reaction chamber 22, such that the reaction between the nanoparticles and the analyte, e.g. target molecule-analyte may occur in the reaction chamber 22. Waste chamber 24 may be vacuum-packed or otherwise packed at a pressure that may be lower than the pressure of reaction chamber 22 and gate 25 may be initially closed (e.g. facilitating a pressure gradient). In one embodiment reaction chamber 22 may be initially filled with liquid that may for example protect the nanocontainers and may provide long term storage capabilities. The reaction chamber 22 may be packaged at atmospheric pressure and/or at a pressure of the in vivo fluid to be sampled. To operate the detection unit, gate 25 may be opened and the pressure gradient between the reaction chamber 22 and waste chamber 24 (waste chamber 24 may be vacuum-packed) may drive the storage liquid from reaction chamber 22 through the capillary tube 23 to waste chamber 24 and the sample to be analyzed into reaction chamber 22 through inlet 21. The gathering of the analyte, e.g. target molecule present in the sample in reaction chamber 22 may cause, for example, rupture of the nanoparticles and/or an optical change in reaction chamber 22. In another embodiment the vacuum in waste chamber 24 may be replaced, for example, by an absorbing agent and a vent to release, for example, the excess of air from waste chamber 24 due to the absorption of the storage liquid. In other examples, more than one waste chamber 24 and gate 25 may be associated with a single reaction chamber 22, so that for example, multiple samples may be drawn into reaction chamber 22. Each of the gates 25 may be controlled separately so that each of the gates may be activated at a separate time. Alternatively more than one gate 25 may be activated simultaneously to draw in a larger volume of a sample. Other configurations of reaction chamber 22, waste chamber 24, gate 25, and tube 23 may be utilized.

Figure 2:
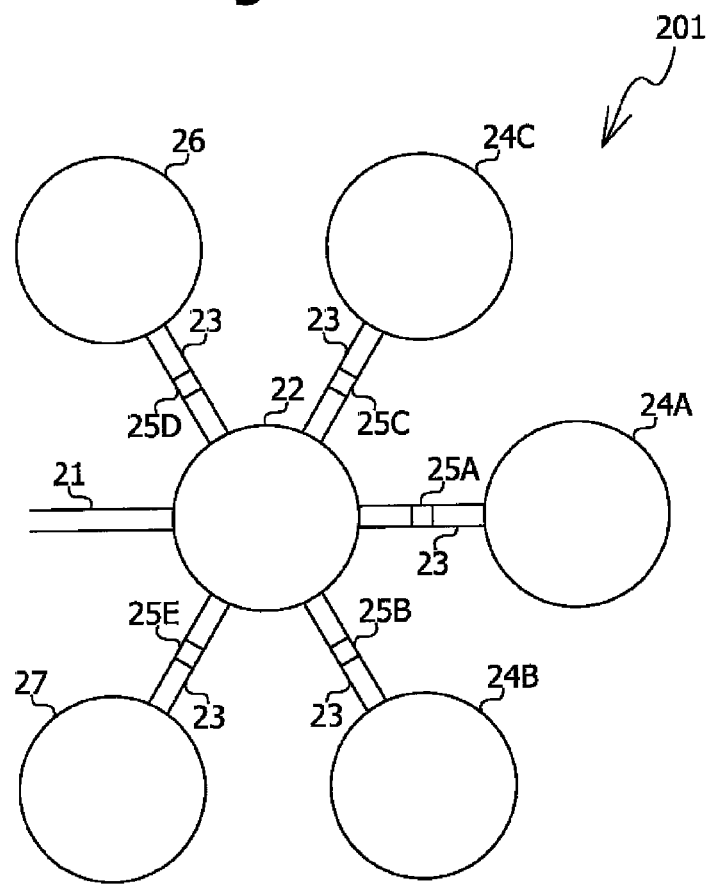
FIG. 2 is a schematic illustration of an alternate detection unit according to another embodiment of the invention.

FIG. 2 is a schematic illustration of an alternate detection unit 201 and/or an alternate basic module of a detection system according to an embodiment of the present invention. According to this embodiment of the present invention, detection unit 201 may include more than one waste chamber 24 and gate 25, e.g. waste chambers 24A, 24B, 24C with corresponding gates 25A, 25B, 25C, that may be associated with for example a single reaction chamber 22. One or more tubes 23 may facilitate passage between each of the waste chambers 24A-C and the reaction chamber 22. Additional chambers, for example, substrate chamber 26, washing solution chamber 27 and or other chambers may also be included in the detection unit 201 and connected with reaction chamber 22 via a tube 23. Each of waste chambers 24A-C may be associated with an inlet 21 or one or more chambers, e.g. substrate chamber 26, washing solution chamber 27, or other chamber that may be designated to dispose at least some of its contents to reaction chamber 22. Multiple inlets 21 may be used. The waste chambers 24A-C together with the gates 25A-C may provide the driving and controlling mechanism for initiating flow in and out of reaction chamber 22.

In some embodiments, one or more reaction chamber 22 may be included in detection unit 201. For example, reaction chamber 22 may have immobilized thereon a detecting reagent, e.g., a tumor specific antibody. The immobilized reagent may be capable of binding a target analyte (for example, the substance of interest in a sample, to be determined by analysis) or a protein that may be used as a market (e.g., a tumor marker) connected to labeled analyte, e.g., an analyte-color compound for example, to detect a disorder. In some embodiments, the immobilized reagent may be capable of binding a labeled analyte, e.g., an analyte-color compound. In some embodiments, after a reaction occurs, for example, after at least a predetermined amount of labeled or non-labeled analyte binds to a detecting reagent in the one or more reaction chamber 22, the sample, which may include, for example, unbound components, may be transported through one of the tubes 23 to one or more of the waste chambers 24A-C.

According to one embodiment of the present invention, the presence of an enzyme in a sample may be determined. Initially an antibody or other binding molecule may be immobilized to reaction chamber 22. Activating or opening gate 25A may facilitate drawing in a sample of an in vivo liquid and/or secretion, for example a sample that may include enzymes, e.g. Pepsin in stomach juice. The enzyme, e.g. the targeted Pepsin present in the sample may adhere to the immobilized antibody and as such the target enzyme may be immobilized to reaction chamber 22. A substrate for the target enzyme stored in chamber 26 may then be passed through reaction chamber 22 by opening gate 25B associated with waste chamber 24B and gate 25D associated with substrate chamber 26. A typically visible enzyme-substrate interaction may occur in reaction chamber 22 when introducing the colored substrate from substrate chamber 26. Typically, after the reaction occurs an optical change may be detected in reaction chamber 22. Typically the rate of change will be proportional to the amount of the immobilized and/or bound enzyme. The sample, which may contain, for example, unbound components, may be washed away by transporting washing solution stored in washing solution chamber 27 through gates 25E and 25C to waste chamber 24C. Washing away unbound components may facilitate optical detection and measurement of the bounded enzymes.

According to some embodiments, one or more waste chambers 24A-C may be vacuum-packed, such that activating one of gates 25A-C between reaction chamber 22 and a vacuum-packed waste chambers 24A-C may facilitate a sample to be transferred to the reaction chamber 22 from the inlet 21 and contents of reaction chamber 22 to be transferred to a corresponding waste chamber 24A-C, e.g., at least due to the pressure gradient between the two chambers. According to other embodiments, one or more waste chambers 24A-C may include an absorbent material, for example, cellulose or absorption pad or other porous material, which may assist in transporting a sample from reaction chamber 22. Waste chambers 24A-C may be ventilated, e.g. by a small hole to enable the release of excess of air to assist absorption. According to some embodiments, tube 23 may assist in the transfer of a sample to the waste chamber 24, for example, due to capillary properties of tube 23 and/or due to applying an appropriate coating of tube 23, e.g., a hydrophobic coating.

In some embodiments, materials suitable for manufacturing detection unit 200 and/or detection unit 201 may be stable to the solutions that may be passed through it.

According to some embodiments, detection unit 200 and/or 201 may include materials capable of binding and/or being coated with special properties, e.g., coating capable of binding, or being derivatized to bind a detecting reagent or a linker to the detecting reagent. Additionally or alternatively, in some embodiments, the material may be selected and/or modified so that it may not substantially bind to the target market or analyte. Some preferred materials, for example, may not bind, or may not otherwise interact, with other components (e.g., color or other labels) whose binding may tend to increase a "background" signal in the assay methods according to embodiments of the invention. Silicon, glass quartz and verity plastic materials are examples of materials that may be used in the construction of detection unit 200 and/or 201 or parts thereof according to some embodiments of the invention. Other minerals or materials may be used, for example, ceramics, metals, paper, metalloids, semi-conductive materials, cements, or the like. Additionally or alternatively, some substances that form gels, (e.g., gelatins), lipopolysaccharides, silicates, agarose polyacrylamides and nitrocellulose may be used for attachment and/or immobilizing the proteins to the chamber. A wide variety of organic and inorganic polymers, both natural and synthetic, may be employed as chamber and/or tube materials. Polymeric materials may form rigid, semi-rigid, or non-rigid, opaque, semi-opaque, or transparent structures, e.g., depending upon the use for which they are intended. For example, units or systems that include an optical or visual detection element may generally be fabricated, at least in part, from transparent materials to allow or at least facilitate such detection.

According to some embodiments, a detecting reagent may be immobilized or affixed to a structure of detection unit 200 and/or 201, e.g., to walls or the floor of reaction chamber 22. In some embodiments, the reaction chamber 22 walls or floor may be derivatized or otherwise treated to be capable of affixing thereon detecting reagents. In other embodiments, detecting reagents may be affixed onto at least part of reaction chamber 22 via a coating of a material that may have functional groups (e.g., amino or acid groups) that can immobilize certain kinds of molecules directly or onto which another layer of binding molecules have been attached via the functional groups, allowing the exposed binding molecules to bind a certain target molecule, e.g. allowing an antigen-antibody binding event to take place.

According to some embodiments, gate 25 may include, for example, one or more pumps or switches, e.g., micro-switches, micro-pumps, Micro Electro Mechanical System (MEMS) switches, MEMS pumps, NEMS (Nano Electro Mechanical System), or the like, which may be controlled automatically, for example, utilizing an internal loop of on-board electronic controller or by an external operator.

According to some embodiments, gate 25 may include dissolvable or meltable materials, for example, waxes, gels, fuses, etc. For example, gate 25 may be opened in a pH dependant manner or a temperature dependant manner, e.g., by use of pH or temperature sensitive materials in constructing the gate 25. In some embodiments, gate 25 may be opened in a time dependant manner; for example, gate 25 may partially or substantially entirely dissolve by a liquid sample in reaction chamber 22, e.g., in accordance with known or calculated kinetics. Upon substantial dissolution of gate 25, there may be substantially unobstructed passage of the sample from the reaction chamber 22 to the waste chamber 24.

According to some embodiments, gate 25 may include a thermal plug. For example, a change of temperature, e.g., from room or environment temperature to body temperature, may cause the gate or plug material (e.g., temperature sensitive hydro gels) to expand or shrink, such that it is pushed out or away of its place, thereby opening or closing a passage between two chambers in detection unit 200.

Figure 3:
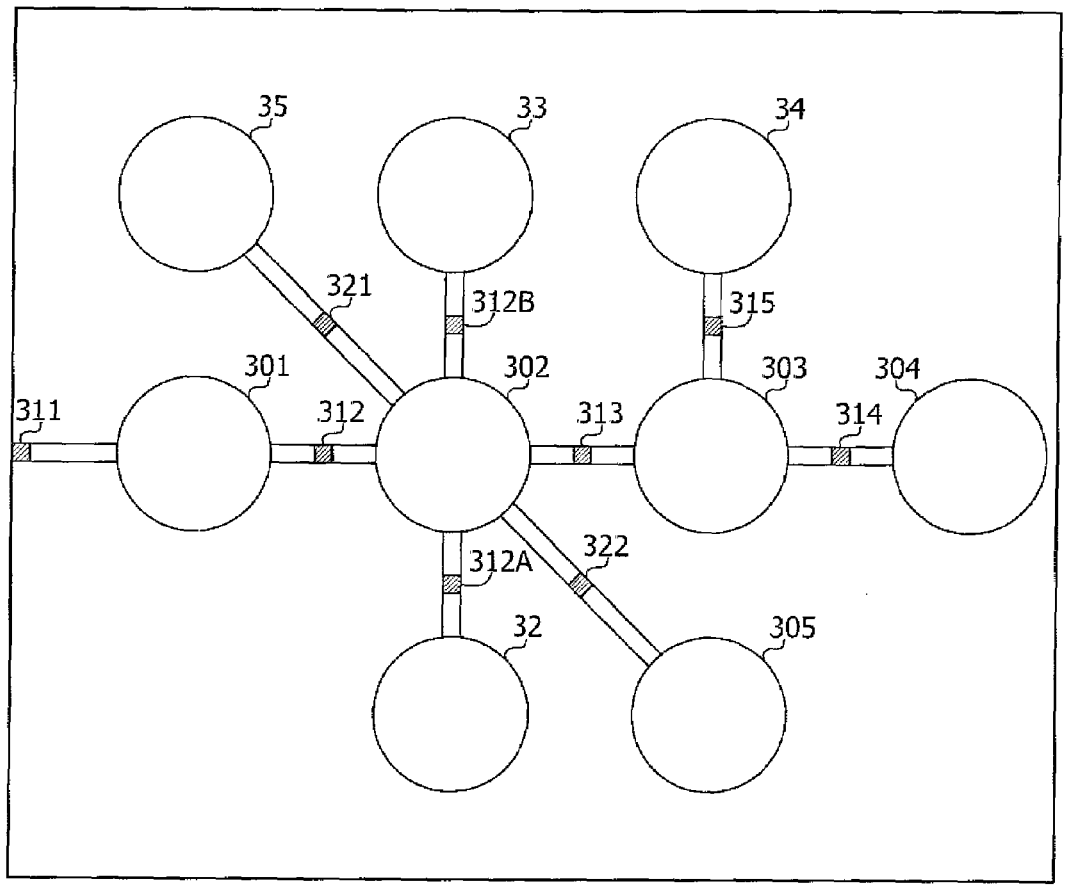
FIG. 3 is a schematic illustration of a detection system according to an embodiment of the invention.

FIG. 3 is a schematic illustration of a detection system 300 according to an embodiment of the invention. Detection system 300, for example, may include one or more detection units 200 and/or 201. Detection system 300 may include addition suitable detection units and/or components.

In accordance with some embodiments, a glass, silicon or other suitable material chip or wafer 30 may include a set of reaction and/or storage chambers and a set of corresponding waste chambers and may be described herein. The reaction and/or storage chambers and waste chambers may be connected through one or more tubes and/or controllable gates as may be described herein. The gates may be opened and/or closed in a controllable manner, e.g., by causing an electrical current through the gate material or through the sample material, by using chemical or other methods of controlling gates (e.g., switches) or other materials suitable for blocking a passage, by using pH sensitive gates, by using temperature sensitive gates, or the like as may be described herein.

In some embodiments, for example, a sample chamber 301 may include a dry buffer, e.g., dry phosphate buffer P3288 available from Sigma-Aldrich (www.SigmaAldrich.com). An inlet 311, e.g. and inlet gate, may open a sample chamber 301 to allow a sample to enter the sample chamber 301. In one example, sample chamber 301 may be vacuum-packed to facilitate drawing in of the sample from the in vivo environment. For example, an endoluminal sample may be collected, and may dissolve the dry buffer in the sample chamber 301, thereby achieving an appropriate solution for a binding reaction (e.g., achieving a desired pH, salt concentration, or the like). Gate 312 and 312A may then be opened, exposing for example vacuum-packed waste chamber 32 so as to drive the buffered sample to pass into a reaction chamber 302. Reaction chamber 302 may include a detection reagent, for example, immobilized onto or in the reaction chamber 302. An analyte and/or a target marker in the buffered sample may bind to the detection reagent and may become affixed in reaction chamber 302.

In some embodiments, an appropriate buffer from a storage chamber 304 may pass through a gate 314 and may enter into a storage chamber 303 that may be vacuum-packed. The storage chamber 303 may include, for example, a labeled detector particle, e.g., a conjugated antibody. The detector particle may be an antigen conjugated to a suitable label, for example, gold particle, colored particle, colored polymer particle, a fluorescent label and/or particle with a fluorescent property, a liposome, a lissome containing a fluorescent material, a liposome containing a colored material, a colored label, a magnetic label, a magnetizable label, a radioactive label, iron-oxide particle, or the like, the conjugate is lyophilized and stored dry to enable long shelf life to the diagnostic kit.

After a predetermined period of time allowing dispersion of labeled particles into buffer to occur in storage chamber 303, a gate 313 and gate 322 may be opened to allow the buffered sample in reaction chamber 302 to be absorbed in waste chamber 305 driving labeled detector particles into reaction chamber 302. The labeled detector particles may be capable of binding the analyte or target marker; accordingly, labeled particles may bind the marker molecules or compounds that may be bound to the immobilized detection reagent in reaction chamber 302. In some embodiments, substantially continuous flow of buffered labeled detector particles from chamber 303 to reaction chamber 302 may be ensured, for example, by opening a gate 312B connecting reaction chamber 302 to an additional waste chamber 33. A second binding reaction may occur in reaction chamber 302, e.g., binding of the labeled particle to the pre-bound analyte or marker.

In some embodiments, the procedure described herein may result in, for example, binding of a detectable label in reaction chamber 302 only if a marker or target analyte was present in the endo-luminal sample. Reaction chamber 302 may be in the field of view of a sensing device, for example, a Charge Coupled Device (CCD) imager, a Complementary Metal Oxide Semiconductor (CMOS) imager; photo-detector, an in vivo imager, or the like. Accordingly, a visibly detectable concentration of label may be imaged or detected by the imager. In one example, an optical system, e.g. an optical system including one or more lens, filters, prisms, etc., to focus an image of at least part of the detection system onto the imager. In some embodiments, images of at least a portion of the content of reaction chamber 302 may be transmitted to a receiving device, e.g., an external receiver/recorder unit outside a patient's body. Other sensing devices may be used in accordance with embodiments of the invention. For example, non-optical detectors or sensors may be used, e.g., fluorescence detectors, radiation detectors, electrical charge detectors, detectors of a change in a magnetic field, or the like. In some embodiments, for example, Hall Effect or Giant Magneto-Resistive (GMR) detectors or sensors may be used, e.g., to detect the presence and/or concentration of antibodies labeled with magnetized particles.

In some embodiments, a piezoelectric device or unit may be attached or integrated into the device, for example, to improve mixing and/or to reduce binding reaction times.

In some embodiments, detection system 300 may be manufactured using suitable fluidics systems constructing techniques. In some embodiments, for example, system 300 may be constructed such that a pressure gradient therein which may be utilized, for example, for transporting fluids between or among chambers of system 300. For example, some embodiments of the present invention may be used in conjunction with one or more embodiments, components, devices and/or methods (e.g., fluidic methods, fluid transportation methods, or the like) described in U.S. Pat. No. 6,453, 928 to Kaplan et al., entitled "Apparatus and Method for Propelling Fluids", which is hereby incorporated by reference in its entirety. In some embodiments, for example, fluids may be transported through chambers using chromatography methods, wicking, bridging, or other suitable methods.

In some embodiments, reactions and/or fluid passage may be facilitated utilizing suitable techniques, for example, by heating a reaction chamber, by vibrating a reaction chamber, or the like. Heating may be performed, for example, utilizing electric and/or chemical based heating methods. Vibration may be caused, for example, by utilizing a piezoelectric crystal, a piezoelectric element or component, and/or magnetostrictive materials (e.g., Terfenol-D). Other suitable methods of heating or vibrating may be used.

In some embodiments, the driving force for transporting liquid from one compartment to the other may be facilitated by vacuum that will suck the liquid once the gate is opened and/or activated. In other embodiments the liquid and/or fluid may be drawn from one chamber to the other by absorption once the gate is activated. In other examples a pressure may be generated (e.g. in a timely manner) to force liquids out of a chamber e.g. by using an electrolysis reaction in a chamber, thereby generating gas in the chamber that may raise the pressure in the chamber, and may thus, for example, force liquids out of the chamber. Other suitable methods may be used according to embodiments of the invention.

For an in vivo sensing device, e.g. in vivo ingestible imaging devices, a typical arrangement may be based on thin layer technologies with chamber dimensions that may range from sub micro-liters to hundreds of micro-liters, typically in the range of 1-10 micro-liters. Other suitable dimensions and sizes may be used.

Figure 4A:
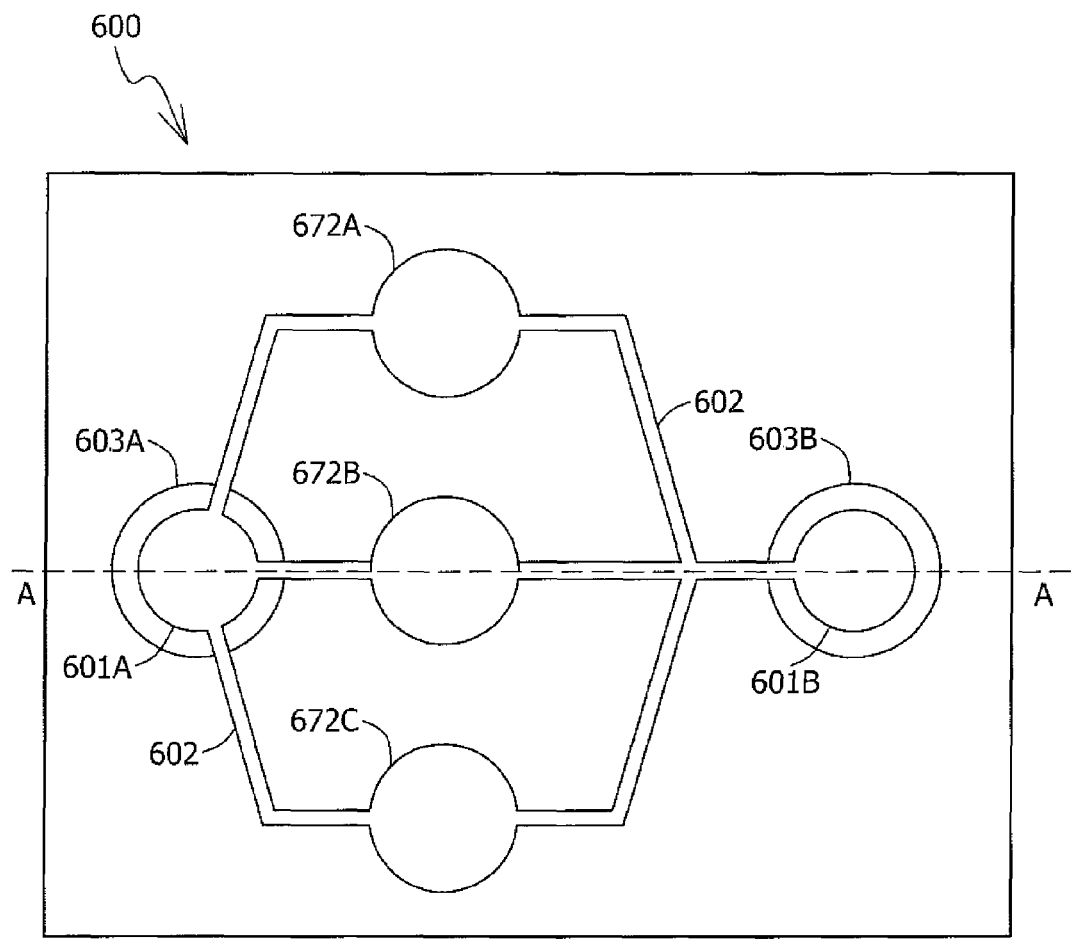
FIG. 4A is a schematic illustration of top view of a micro-fluidic detection system based on said thin layer technology according to an embodiment of the invention.
Figure 4B:
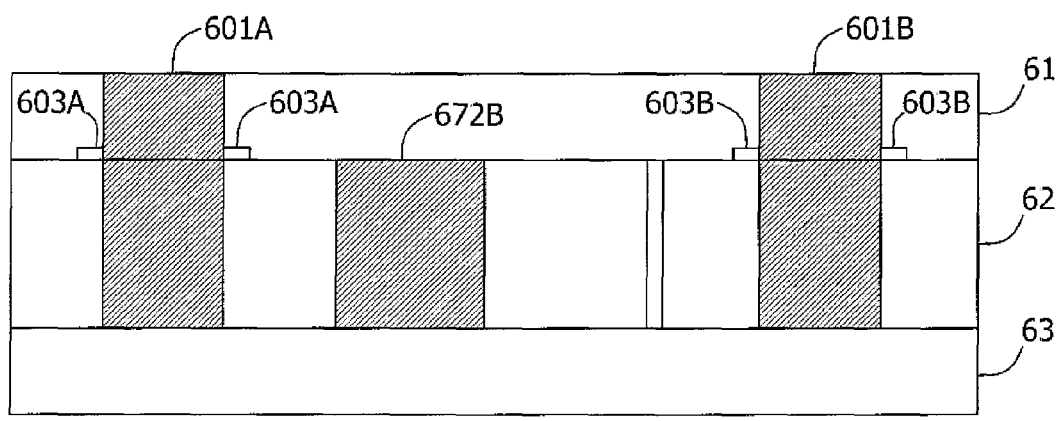
FIG. 4B is a schematic illustration of a cross sectional view of micro-fluidic detection system based on said thin layer technology according to another embodiment of the invention.

Reference is now made to FIGS. 4A and 4B showing a schematic top and cross sectional view of a micro-fluidic detection system based on said thin layer technology. In some embodiments, detection system 600 may be relatively easy to manufacture, and/or may require minimum passage space for the samples being transferred through the detection system 600. Such micro-fluidic detection systems 600 may include but may not be limited to a substrate 63 made of silicon wafer with a typical thickness of approximately and/or in the order of magnitude of 0.5 mm or a slab of glass or a slab of plastic or any other suitable material. Other dimensions may be used. A cover 61 and spacer 62 may be bonded or adhered to the substrate 63 and may be constructed with one or more of the materials described herein, a combination of materials, or any suitable materials known in the art. The substrate may be a multi-layered substrate. In some embodiments, the dimensions of the chambers and/or passages may be as small as possible, consistent with ease of handling and mechanical stability, to reduce the amount of sample required for an assay. Dimensions may range, for example, from a characteristic dimension of about 10 micron to about 1000 micron. Liquid volumes of, for example, from about 1 micro-liter to about 100 micro-liters may be transferred through a system according to some embodiments of the invention. Other sizes and volumes may be used.

In some embodiments, micro-fluidic detection system 600 may be used to detect a variety of markers or targeting agents. The micro-fluidic detection system 600 in FIGS. 4A and 4B may include, for example, a cover layer 61 that may be fabricated from, for example, plastic or glass or any other suitable transparent material and may be glued or bonded to a spacer 62. The cover layer 61 may have corresponding openings 601A and 601B that may be sealed with for example, a pH sensitive or a temperature sensitive material creating a gate, that may be opened only when the in vivo device may reach a desired destination e.g. for an ingestible in vivo device, the cover may be made of a paraffin material dissolving at a specific temperature, e.g. body temperature or temperature of 36 degree Celsius such that it may open in vivo. In another example, the gate may be fabricated by gelatin or similar pH sensitive material that may dissolve only when the in vivo device may reach, for example, the acidic stomach. In yet another example, the gate may be sealed with wax or plastic like. Polyvinylidene Chloride (PVDC) that may melt when the gate is heated with a heater (e.g. a coil and/or heating element 603A and 603B may be constructed of a heat conducting material, e.g. aluminum that may be operatively connected to a power source like a battery or charged capacitor and a controller that may operate the coils 603A and 603B at a desire time or location). Channels 602 and reaction chambers 672A-C may be formed, for example by cutting suitable slits in spacer 62 using methods known in the art. By bonding or gluing the spacer 62 to a substrate 63 below and to the covers 61 above, a hollowed cannel may be formed creating both: fluidic communications 602 and the reaction chambers 672A-C. More or less chambers may be used. In some embodiments the driving force for driving the sample into the chambers may be capillary forces. In such cases air should be released e.g., through a hole 601B that may be opened along with inlet opening 601A.

Figure 4C:
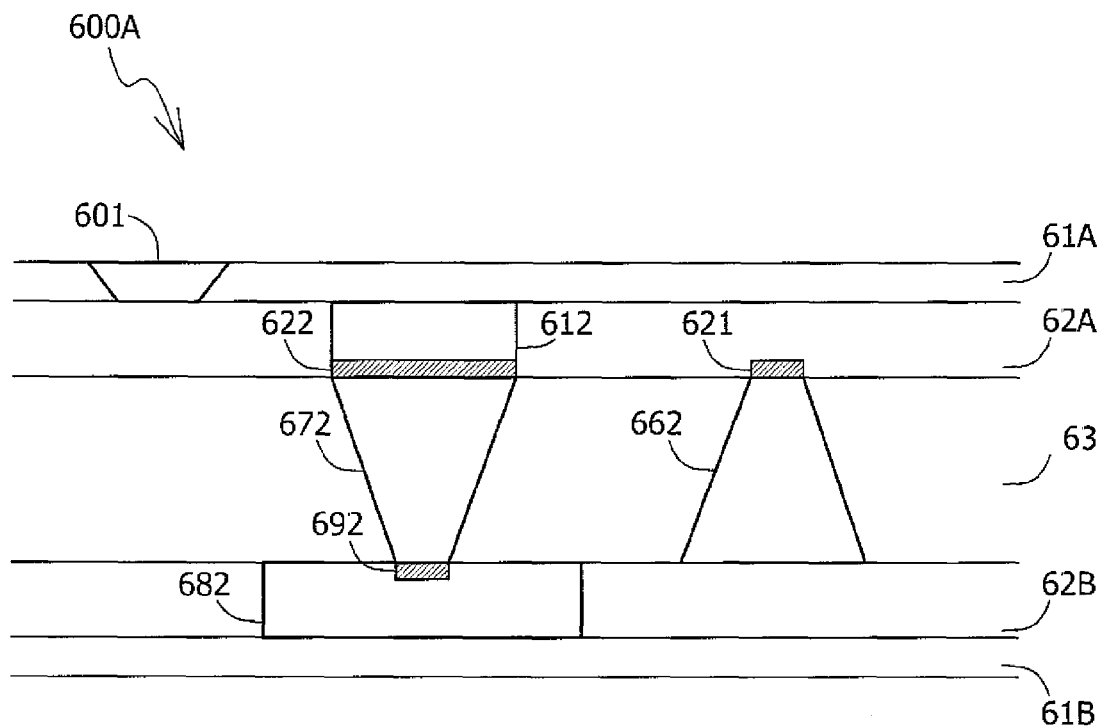
FIG. 4C is a schematic illustration of a multilevel detection system according to an embodiment of the invention.

Reference is now made to FIG. 4C showing a cross sectional view of micro-fluidic detection system 600A based on said thin layer technology according to another embodiment of the invention. In FIG. 4C one or more storage chambers 612 accompanied by one or more vacuum-packed waste chambers 662 with one or more gates 621 that may be used to facilitate entrance of the in vivo sample through hole 601 into sample chamber 612 as may have been described herein. Alternatively, storage chambers 612 may be vacuumed packed and include a gate that may be opened to allow the in vivo sample to enter through opening 601 and collect in one or more sampling chambers 612.

In some embodiments substrate 63 may be made of silicon with pad oxide layer grown on one or both side, e.g. a side facing 62B, using standard oxidation techniques, on the oxide layer a silicon nitride layer may be formed using standard Low Pressure Chemical Vapor Deposition (LPCVD) technique. Other techniques may be used. Chambers and or cavities, e.g. waste chamber 662 and reaction chamber 672 may be formed by using standard silicon lithography and etching methods well known in the art. A layer of about 1 micron of aluminum or another suitable layer of electrically resistive material may be applied. By using lithographic methods well known in the art an electrical heater may be formed just below reaction chamber 672. Spacer 62B with an outlet to waste chamber 682 may be produced using standard thin layer technology. By gluing or bonding the silicon wafer 63 to spacer 62B and cover 61B in a vacuumed chamber, an airless, or vacuum-packed waste chamber 682 may be formed together with a gate 692. The heater of the gate 692 may be thermally coupled to the brittle silicon nitride, heating the thin nitride layer will create a mechanical stress that will breach the sealing layer and the gate may be opened, e.g., to allow air or sample from reaction chamber 672 to move into waste chamber 682.

On the upper side of the silicon for example a polymeric sealing layer like Kapton® or PVDC or any other suitable sealing layer can be used. This sealing layer may also be coated with aluminum or other thermal heater as described above and bonded to spacer 62A. A variety of analysis materials like dry buffers, lyophilized conjugated liposomes, or any other conjugates and/or immobilized antigens or targeting agents can be applied to both reaction chambers 672 and sample chambers 612. The final assembly is created by gluing or bonding the cover 61A to spacer 62A and spacer 62A with the cover and sealing layer to silicon wafer 63. In a preferred embodiment the final bonding may also be made in a vacuum, turning also storage chamber 612 and reaction chamber 672 into vacuum-packed chambers. In another embodiment, more than 3 sets of chambers may be produced in parallel. According to one embodiment of the present invention, more than one storage chamber 612 may be used and more than one reaction chamber 672 may be used to substantially simultaneously test for different analytes in a sample. For example, a plurality and/or matrix of storage chambers 612, reaction chambers 672, and waste chambers 662 and 682 may be included in a single detection unit 601.

In a preferred embodiment one or more storage chambers 612 may contain dry buffer with dry or lyophilized antibody conjugate. The conjugate may be based on gold particles. Other colored particles, liposomes or polymersones filled with detecting substances (e.g. fluoresces materials) may be used. In other embodiments iron oxide or other paramagnetic particles may be used. Each chamber may have a different antibody or targeting agent reacting to different analyte or different disorder. One or more reaction chamber 672 may contain reagent immobilized to the chamber walls of the reaction chamber 672, such that a binding reaction may occur between the said reagent and a congregate analyte that may be present in the sample entering from chamber 612.

One of a plurality of storage chambers 612 may act as a reference or calibration and may include, for example, standard antibody-antigen-congregate at a predetermined concentration at storage 612 to serve as a reference.

In a preferred embodiment detection system 600 may be part of an in vivo device, e.g. an ingestible imaging device. After the ingestible imaging device is swallowed and penetrates into the stomach, the gelatin comprising gate 601A and 601B may come in contact with stomach juices and dissolve. As a result the stomach juices may enter through an opening 601 and reach one or more sample chambers 612. The buffer stored in those sample chambers 612 may be dissolved enabling the reaction between targeted agents that may be present in the sample and the conjugates. At a predetermined time, the heating element 603A and 603B at one or more gates 622 may be activated and may open one or more gates 622. The solution containing detection particles (e.g., target-antibody-color conjugate) may be transferred from one or more sample chambers 612 to one or more reaction chambers 672 to allow reaction of the target-antibody—conjugates with the immobilized reagents of one or more reaction chambers 672. After another period of time to allow the reaction to be accomplished opening of a gate 692 may allow the liquid from reaction chamber 672 to be sucked into one or more waste chambers 682. The reactions that may occur in one or more reaction chambers 672 may result in an indication of the presence and/or concentration of an analyte in the sample. The color change of the walls of the reaction chamber 672 located below chamber 612 that contained the standard antibody-antigen-congregate at a predetermined concentration, e.g. the reference reaction chamber, may represent a color change of a known concentration. By comparing the intensity of the color change of that reference reaction chamber 672 to the color change in other reaction chambers 672 quantitative data can be obtained.

Optionally, a mixing element, for example, a piezoelectric element, may be added to the detection device to facilitate mixing.

In some embodiments, one or more reaction chambers 672, or a portion thereof, may be, for example, in an optical path or in the field of view of a photo detector, imager or an image sensor, e.g., an in vivo imager, which may acquire one or more images. Additionally or alternatively, one or more reaction chambers 672 or its content, or a portion thereof may be exposed to a non-optical sensor or detector, e.g., to detect or sense the presence of an analyte, for example, by change in magnetic field when paramagnetic particles are used in the conjugate.

Figure 5:
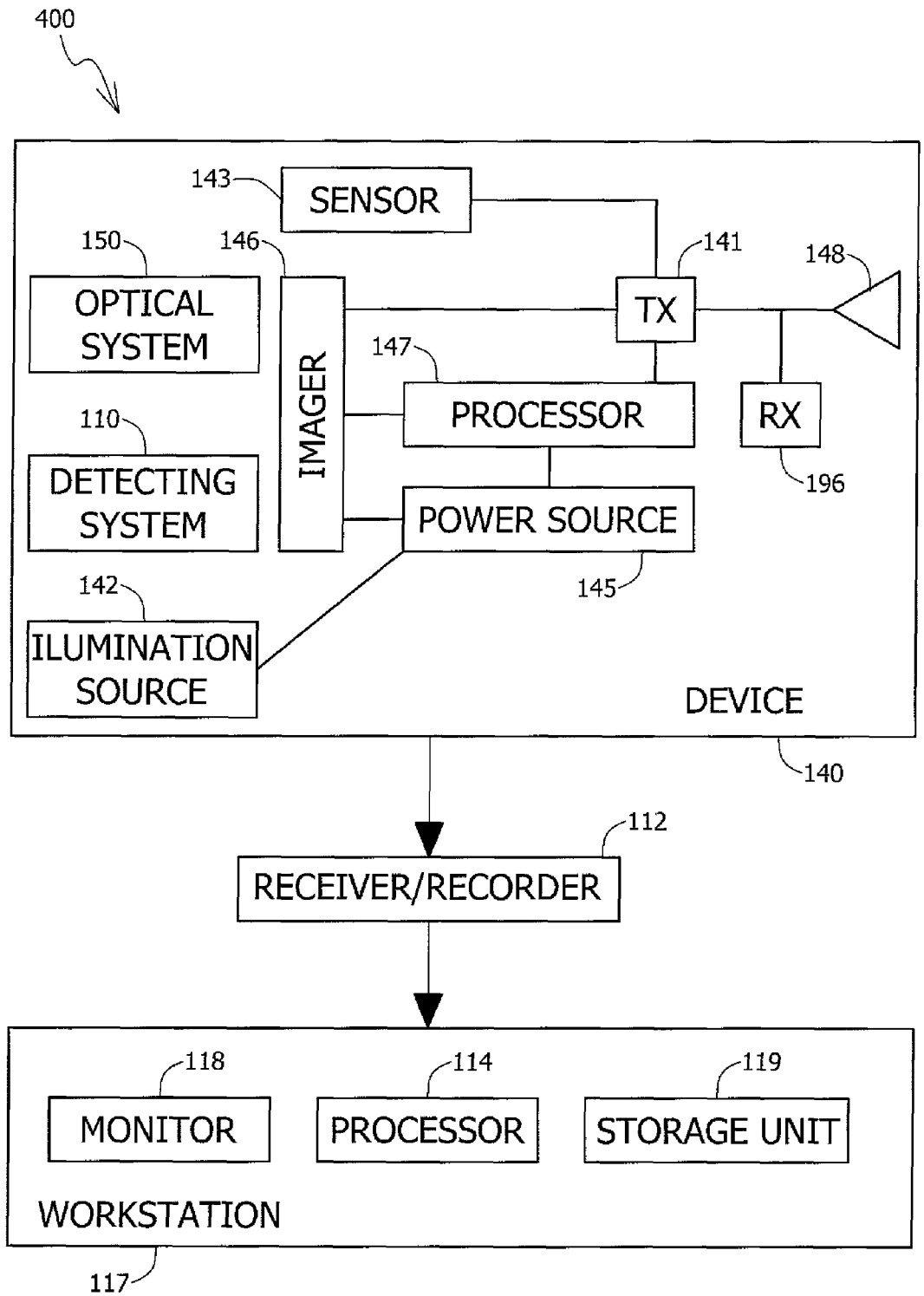
FIG. 5 is a schematic illustration of an in vivo sensing device and system according to an embodiment of the invention.

FIG. 5 is a schematic illustration of an in vivo sensing system 400 according to an embodiment of the invention. One or more components of system 400 may be used in conjunction with, or may be operatively associated with, the devices and/or components described herein or other in vivo devices in accordance with embodiments of the invention.

In some embodiments, system 400 may include an in-vivo device, e.g. ingestible device 140 having a sensor, e.g., an imager 146, one or more illumination sources 142, a power source 145, and a transmitter 141. In some embodiments transmitter 141 may be replaced by a transceiver and/or a receiver 196 may be included within ingestible device 140 to receive commands from an external source. In some embodiments, ingestible device 140 may be implemented using a swallowable capsule. In another embodiment ingestible device 140 may be an implant inserted by minimal invasive techniques but other sorts of devices or suitable implementations may be used.

Ingestible device 140 typically may be or may include an autonomous swallowable capsule, but ingestible device 140 may have other shapes and need not be swallowable and/or autonomous. Embodiments of ingestible device 140 are typically autonomous, and are typically self-contained. For example, ingestible device 140 may be a capsule or an implant or other unit where all the components are substantially contained within a container or shell, and where ingestible device 140 does not require any wires or cables to, for example, receive power of transmit information. In some embodiments, ingestible device 140 may be autonomous and non-re more-controllable; in another embodiment, ingestible device 140 may be partially or entirely remote-controllable.

Outside a patient's body may be, for example, an external receiver/recorder 112, which may include, or may be associated with, one or more antennas (or antenna elements), optionally arranged as an antenna array. Receiver/recorder 112 may receive signals transmitted by the in vivo ingestible device 140, for example, signals carrying image data, sensed data, control data, or the like. Receive/recorder 112 may, for example, store the received data in a memory unit or a storage unit, or may display the information on a display unit (e.g., in real time or not in teal time), for example, using hand-held device or computer. In other embodiments receiver/recorder 112 may include a transmitter as well as a receiver and/or a transceiver for receiving as well as transmitting information to ingestible device 140.

Additionally, outside a patient's body may be, for example, a storage unit 119, a processor 114, and a monitor 118. In some embodiments, for example, processor 114, storage unit 119 and/or monitor 118 may be implemented as a workstation 117, e.g., a computer or a computing platform. Workstation 117 may be connected to receiver/recorder 112 through a wireless or wired link or connection. Workstation 117 may receive from receiver/recorder 112 data that is received and/or recorded by receiver/recorder 112. In some embodiments, workstation 117 may receive the data from receiver/recorder 112 substantially in real-time, and/or while receiver/recorder 112 continues to receive and/or record data from the in vivo ingestible device 140.

Transmitter 141 may operate using radio waves; but in some embodiments, such as those where ingestible device 140 is or is included within an endoscope, transmitter 141 may transmit/receive data via, for example, wire, cable, optical fiber and/or other suitable methods. Other known wireless methods of transmission may be used. Transmitter 141 may include, for example, a transmitter module or sub-unit and a receiver module or sub-unit, or an integrated transceiver or transmitter 141 and receiver 196.

In some embodiments, device 140 may optionally include a receiver 196, for example, a wired or wireless (e.g., RF) receiver, able to receive signals from an external transmitter. The received signals may include, for example, control signals or commands, e.g., to activate and/or otherwise control one or more components of device 140. Receiver 196 may receive signals, e.g., from outside the patient's body, for example, through antenna 148 or through a different antenna or receiving element. In some embodiments, signals or data may be received by a separate receiving unit in device 140. In some embodiments, transmitter 141 and receiver 196 may optionally be implemented using a transceiver unit or an integrated transmitter-receiver unit.

In some embodiments, ingestible device 140 may communicate with an external receiving and display system (e.g., workstation 117 or monitor 118) to provide display of data, control, or other functions. For example, power may be provided to ingestible device 140 using an internal battery, a charged capacitor or any other internal power source, or a wireless system able to receive power. Other embodiments may have other configurations and capabilities. For example, components may be distributed over multiple sites or units, and control information or other information may be received from an external source.

In some embodiments, ingestible device 140 may include an in vivo video camera, for example, imager 146, which may capture and transmit images of, for example, the GI tract while ingestible device 140 passes through the GI lumen. Other lumens and/or body cavities may be imaged and/or sensed by ingestible device 140. In some embodiments, imager 146 may include, for example, a Charge Coupled Device (CCD) camera or imager, a Complementary Metal Oxide Semiconductor (CMOS) camera or imager; a solid-state camera or imager, a linear imaging sensor, a line imaging sensor, a full flame imaging sensor, a "camera on chip" imaging sensor, a digital camera, a stills camera, a video camera, or other suitable imagers, cameras, or image acquisition components.

In some embodiments, imager 146 in ingestible device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in some embodiments, transmitter 141 may include an ultra low power Radio Frequency (RF) high bandwidth transmitter, possibly provided in Chip Scale Package (CSP).

In some embodiment, transmitter 141 may transmit/receive via antenna 148. Transmitter 141 and/or another unit in ingestible device 140, e.g., a controller or processor 147, may include control capability, for example, one or more control modules, processing module, circuitry and/or functionality for controlling ingestible device 140, for controlling the operational mode or settings of ingestible device 140, and/or for performing control operations or processing operations within ingestible device 140. According to some embodiments, transmitter 141 may include a receiver which may receive signals (e.g., from outside the patient's body), for example, through antenna 148 or through a different antenna or receiving element. According to some embodiments, signals or data may be received by a separate receiving device in ingestible device 140.

Power source 145 may include one or more batteries or power cells. For example, power source 145 may include silver oxide batteries, lithium batteries, other suitable electrochemical cells having a high energy density, or the like.

Other suitable power sources may be used. For example, power source 145 may receive power or energy from an external power source (e.g., an electromagnetic field generator), which may be used to transmit power or energy to in vivo ingestible device 140.

In some embodiments, power source 145 may be internal to ingestible device 140, and/or may not require coupling to an external power source, e.g., to receive power. Power source 145 may provide power to one or more components of ingestible device 140 continuously, substantially continuously, or in a non-discrete manner or timing, or in a periodic manner, an intermittent manner, or an otherwise non-continuous manner. In some embodiments, power source 145 may provide power to one or more components of ingestible device 140, for example, not necessarily upon-demand, or not necessarily upon a triggering event or an external activation or external excitement.

Optionally, in some embodiments, transmitter 141 may include a processing unit or processor or controller; for example, to process signals and/or data generated by imager 146. In another embodiment, the processing unit may be implemented using a separate component within ingestible device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 141, and may be implemented, for example, using an ASIC.

In some embodiments, imager 146 may acquire in vivo images continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 141 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, ingestible device 140 may include one or more illumination sources 142, for example one or more Light Emitting Diodes (LEDs), "white LEDs", monochromatic LEDs, Organic LEDs (O-LEDs), thin-film LEDs, an emissive electroluminescent layer or component, Organic Electro-Luminescence (OEL) layer or component, or other suitable light sources. Illumination sources 142 may, for example, illuminate a body lumen or cavity being imaged and/or sensed. An optional optical system 150, including, for example, one or more optical elements, lenses, composite lens assemblies, magnifying lens, optical filters, prisms, gratings, plane mirrors, curved mirrors, concave mirrors or elements, convex mirrors or elements, reflective surfaces, reflective elements, light tunnels, light diverting elements, light focusing elements, or any other suitable optical elements, may optionally be included in ingestible device 140. Optical system 150 may, for example, aid in focusing reflected light onto imager 146, focusing illuminated light, and/or performing other light processing operations.

In some embodiments, illumination source(s) 142 may illuminate continuously, or substantially continuously, for example, not necessarily upon-demand, or not necessarily upon a triggering event or an external activation or external excitement. In some embodiments, for example, illumination source(s) 142 may illuminate a pre-defined number of times per second (e.g., two or four times), substantially continuously, e.g., for a time period of two hours, four hours, eight hours, or the like; or in a periodic manner, an intermittent manner, or an otherwise non-continuous manner.

In some embodiments, the components of ingestible device 140 may be enclosed within a housing or shell, e.g., capsule-shaped, oval, or having other suitable shapes. The housing or shell may be substantially transparent or semi-transparent, and/or may include one or more portions, windows or domes (e.g., a dome-shaped window) which may be substantially transparent or semi-transparent. For example, one of more illumination source(s) 142 within ingestible device 140 may illuminate a body lumen through a transparent or semitransparent portion, window or dome; and light reflected from the body lumen may enter the ingestible device 140, for example, through the same transparent or semi-transparent portion, window or dome, or, optionally, through another transparent or semi-transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

Data processor 114 may analyze the data received via external receiver/recorder 112 from ingestible device 140, and may be in communication with storage unit 119, e.g., transferring frame data to and from storage unit 119. Data processor 114 may provide the analyzed data to monitor 118, where a user (e g, a physician) may view or otherwise use the data. In some embodiments, data processor 114 may be configured for real time processing and/or for post processing to be performed and/or viewed at a later time. In the case that control capability (e.g., delay, timing, etc) is external to ingestible device 140, a suitable external device (such as, for example, data processor 114 or external receiver/recorder 112 having a transmitter or transceiver) may transmit one or more control signals to ingestible device 140.

Monitor 118 may include, for example, one or more screens, monitors, or suitable display units. Monitor 118, for example, may display one or more images or a stream of images captured and/or transmitted by ingestible device 140, e.g., images of the GI tract or of other imaged body lumen or cavity. Additionally or alternatively, monitor 118 may display, for example, control data, location or position data (e.g., data describing or indicating the location or the relative location of ingestible device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, ingestible device 140 may transmit image information in discrete portions. Each portion may typically correspond to an image or a frame; other suitable transmission methods may be used. For example, in some embodiments, ingestible device 140 may capture and/or acquire an image once every half second, and may transmit the image data to external receiver/recorder 112. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. According to other embodiments a 320×320 pixel imager may be used. Pixel size may be between 5 to 6 microns; other suitable sizes may be used. According to some embodiments, pixels may be each fitted with a micro lens. For example, a Bayer color filter may be applied. Other suitable data formats may be used, and other suitable numbers or types of tows, columns, arrays, pixels, sub-pixels, boxes, super-pixels and/or colors may be used.

Optionally, ingestible device 140 may include one or more sensors 143, instead of or in addition to a sensor such as imager 146. Sensor 143 may, for example, sense, detect, determine and/or measure one or more values of properties or characteristics of the surrounding of ingestible device 140. For example, sensor 143 may include a pH sensor, a temperature sensor, an electrical conductivity sensor, a pressure sensor, or any other known suitable in vivo sensor.

In some embodiments, ingestible device 140 may be, for example, an oblong, oval, or spherical capsule, and/or may be swallowable and/or autonomous; other dimensions and/or configurations may be used. In other embodiments ingestible device 140 may be a flat implant with numerous amount of analysis sets adjusted for under skin implantation.

In some embodiments, ingestible device 140 may include an analyzing or detecting system 110. Detecting system 110, may be part of or may be constructed on, a wafer or chip, e.g., on a silicon, glass or plastic wafer. Detecting system 110 may sample the in vivo environment, for example, by collecting a sample of, e.g., endo-luminal liquid or cells or tissue. The in vivo sample, and/or any market that the sample may include, may be reacted with a detecting reactant which may be included within the detecting system 110. A reaction between a marker and a detecting reactant may be optically visible and may be imaged, for example, by imager 146. Images acquired by imager 146 may include data relating to a reaction in detecting system 110. The images may be transmitted by transmitter 141 to receiver/recorder 112, and may be processed and displayed, for example, using workstation 117.

In some embodiments, detecting system 110 may be positioned or located in the in vivo ingestible device 140 within the field of view of the imager 146, for example, under a window or dome of the in vivo ingestible device 140. In some embodiments, for example, imager 146 may be able to acquire images of at least a portion of the reaction result, or an image of at least a portion of a reaction chamber of detecting system 110. In other embodiments, for example, imager 146 may be able to acquire images of a body lumen. In still other embodiments, for example, imager 146 may be able to acquire images showing both a portion of a body lumen and a portion of the reaction result and a portion of the reaction chambers.

In some embodiments, ingestible device 140 may include other suitable detection means, for example, as described herein, and signals other than signals carrying image data may be transmitted by transmitter 141.

In some embodiments, a marker or target analyte may include an antigenic determinant, for example, antigen bearing cells, e.g., cancerous cells, viruses, bacteria, fingi, other parasites; or an antibody that may be present in a body lumen, for example, antibodies produced in response to a viral or bacterial attack or in response to the presence of a tumor or other pathologies. In some embodiments, a marker may further include substances, for example, chemical or biological determinants, having affinity to a detecting reactant. A detecting reactant may be, for example, a molecule or compound capable of binding a marker. For example, detecting reagents may include proteins, e.g., antibodies, nucleic acids, or other biological or synthetic polymers. Other suitable substances or materials may be used.

In some embodiments, a reaction may take place within detecting system 110, which may include a first (e.g., typically colored) detecting reagent adhering to a marker in a sample, and a marker-color compound adhering to a second (e.g., typically immobilized) detecting reagent. Other types of reactions may occur. In some embodiments, the adhering of the marker-color compound to the second reagent may form a visible (e.g., colored or otherwise optically obscuring) marking. In some embodiments, visible reactions may be similar to, for example, pregnancy detection kits which utilize a marker-color compound reaction with a second immobilized detecting reagent. In some embodiments, other detection methods may be used, for example, agglutination procedures.

In some embodiments, a typically cancerous marker; for example, CarcinoEmbryonic Antigen (CEA) or CA-19.9 or alike may be detected in GI tract fluids, e.g., using labeled antibodies as detecting reagents. In some embodiments, different types of Pepsin, and different types of Gastrin may be detected in the stomach. For example, using colored material consumed by the Pepsin enzyme or by using antibody/antigen reaction. In some embodiments, Nitric oxide (NO) may be detected, for example, using color change or pH sensitive reagents. Other materials or substances may be senses and/or used.

In some embodiments, for example, a gate may include elements and/or materials that may be heated to shrink and/or expand and or melt, thereby clearing or filling in a passage or a tube between chambers and enabling and/or disabling passage of fluids through that passage or tube. Such elements or materials may include, for example, fuses, reeds, waxes, silicone oxide and nitrides, air bubbles, bubbles produced by electrolysis, and/or other suitable substances.

In some embodiments, opening and/or closing of gates may be active, e.g., in response to an external command; and/or passive, for example, in reaction to certain environmental conditions, e.g., temperature, pH, moisture, pressure, or the like.

Although portions of the description herein may relate, for demonstrative purposes, to gates, embodiments of the invention are not limited in this regard; for example, a gate may include, or may be implemented using, a tube or passage which may be opened and/or closed, a tube or passage which may be enabled or disabled, a barrier, a dissolvable element, a semi-dissolvable element, a blocking element which may be introduced or removed, a shutting or closing element which may be introduced or removed, a valve, a one-way or a two-way gate or valve, a one-way or two-way tube or passage, or the like.

Figure 6A:
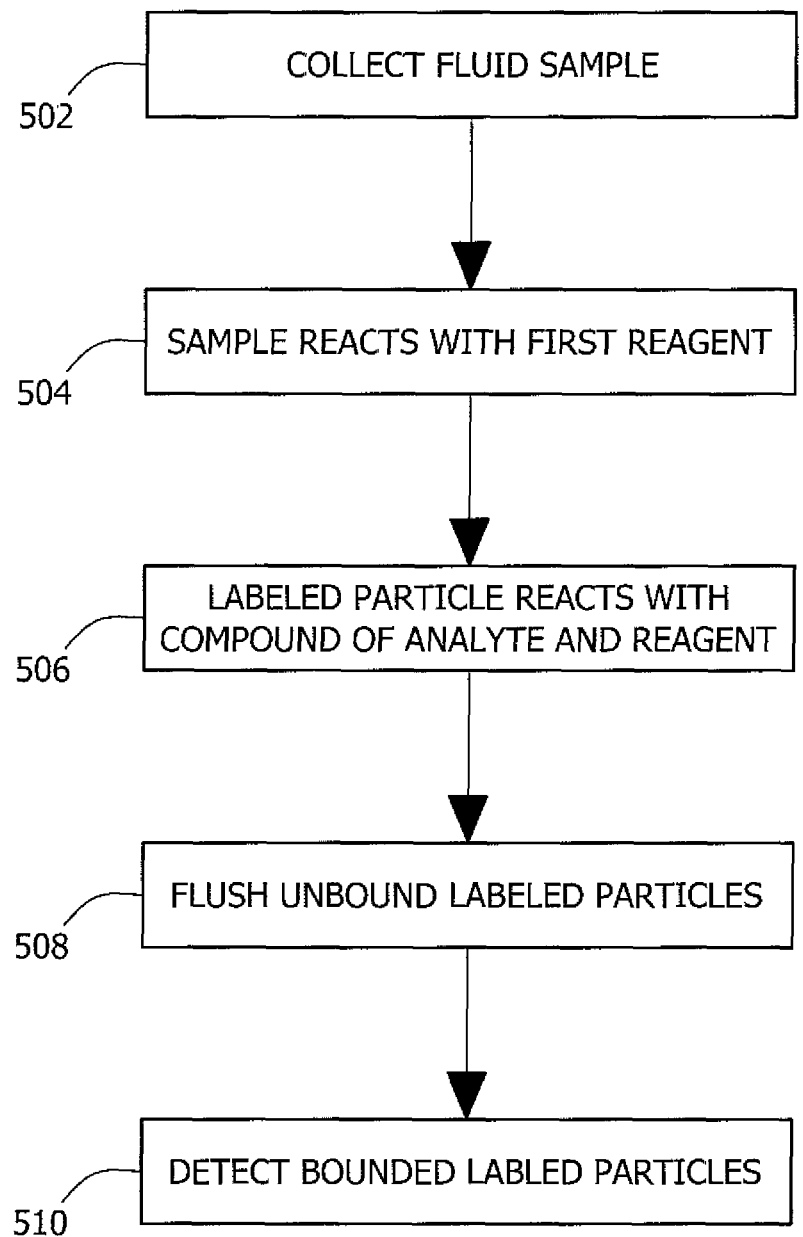
FIG. 6A is a flowchart depicting a method for in vivo analysis according to an embodiment of the invention.

FIG. 6A is a flowchart depicting a method for a diagnostic analysis according to an embodiment of the invention. In some embodiments, an in vivo device is used (e.g., an autonomous in vivo device, a swallowable capsule, implant or the like). In said embodiments one or some or all of the operations of the method may be performed in vivo, and/or while the in vivo device is within a patient's body. In some embodiments, for example, one or more operations may be performed in vivo, and one or more operations may be performed in vitro or ex vivo.

As indicated in box 502, a fluid sample (e.g., a sample from the GI tract) may be gathered or collected in vivo.

As indicated in box 504, the in vivo sample may be reacted with a first detecting reagent, for example, to obtain binding of a marker, if present in the sample, to the first detecting reagent. In some embodiments, the first detecting reagent may be unlabeled, and may be affixed to a certain location, for example, to a reaction chamber in an in vivo sensing or imaging device.

As indicated in box 506, a typically labeled particle may be reacted with the compound of the analyte and/or marker and the first detecting reagent. This may be performed, for example, by binding of the labeled particle to the typically immobilized compound of the marker and the first detecting reagent.

As indicated in box 508, flushing or washing of the labeled particle may be performed by opening a gate of a washing solution chamber and a waste chamber so that the excess unbounded labeled particles may be flushed into the waste chamber.

As indicated in box 510 the binding of the labeled particles to the immobilized compound may be detected, for example, by imaging or otherwise sensing the label, thereby indicating the presence and/or concentration of a marker in the sample.

Figure 6B:
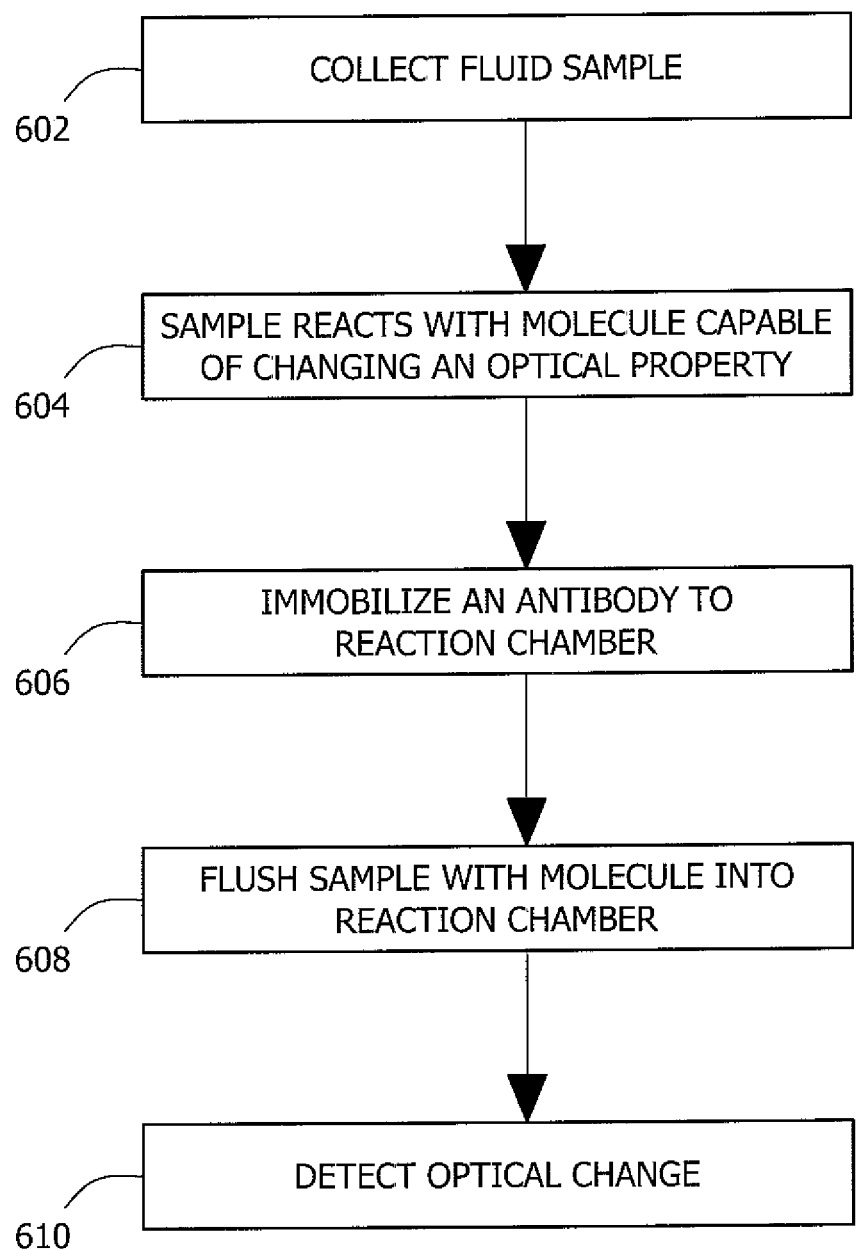
FIG. 6B is a flowchart depicting a method for in vivo analysis according to another embodiment of the invention.

Reference is now made to FIG. 6B showing a flowchart depicting a method for analysis according to another embodiment of the invention.

As indicated in box 602, a sample (e.g., a sample from the GI tract) may be gathered or collected in vivo.

As indicated in box 604, the sample may be reacted with a molecule capable of changing optical properties of a substrate.

As indicated in box 606, an antibody, or other binding molecule for the target analyte, may be immobilized to a reaction chamber such that the tar get analyte may adhere to the antibody and the molecule attached to it will essentially be immobilized to the reaction chamber when the molecule-analyte containing sample passes through the reaction chamber 22.

As indicated in box 608, the molecule with the sample may be flushed into the reaction chamber and the gathering of the molecule in reaction chamber 22 may cause, for example, an optical change in reaction chamber that may be detected, for example, by imaging or otherwise sensing the label, thereby indicating the presence and/or concentration of a marker in the sample.

As indicated in box 610, the optical change may be detected, by for example an image captured by an imager, the output of a photo-detector, or by other suitable means. For in-vitro applications the optical change may be detected by the human eye.

Other detection methods may be used, for example, detection of magnetic particles using a magnetic field change detector. Other suitable operations may be used.

Figure 6C:
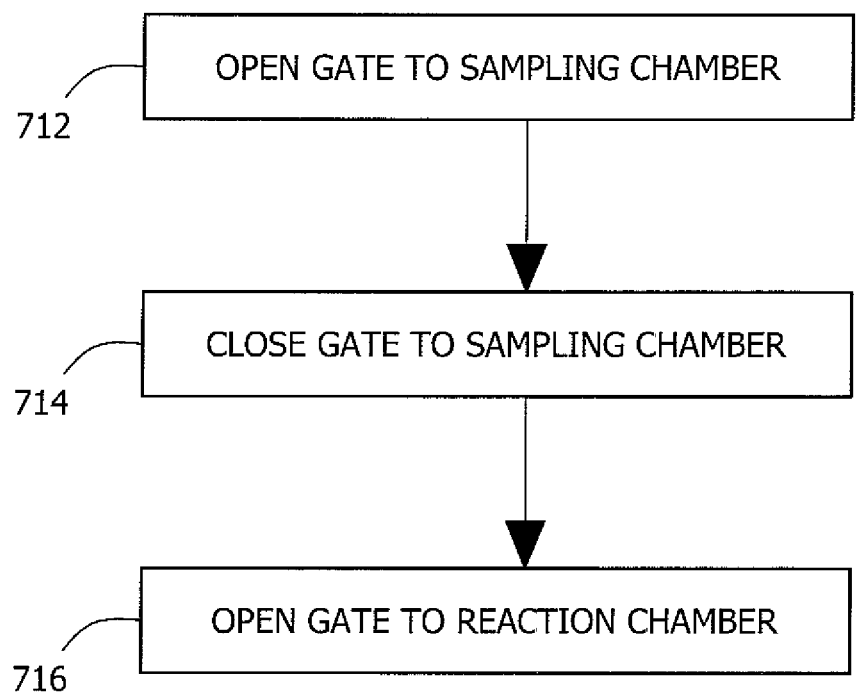
FIG. 6C is a flowchart depicting a method for in vitro analysis according to an embodiment of the invention.

FIG. 6C is a flowchart depicting a method for in vitro analysis according to an embodiment of the invention. In some embodiments, one or some or all of the operations of the method may be performed in-vitro, ex-vivo, outside a patient's body, at the physician office, in a laboratory, or the like. In some embodiments, for example, one or more operations may be performed in vivo, and one or more operations may be performed in vitro or ex vivo.

As indicated in box 712, a first gate between a sample reservoir and a sampling chamber may be opened, thereby enabling a sample to be drawn into the sampling chamber.

As indicated in box 714, the first gate between the sampling chamber and the sample reservoir may be closed, thereby stopping the sampling (e.g., ending the sample collection) and isolating the sampling chamber from the sample reservoir.

As indicated in box 716, a second gate may be opened between the sampling chamber and a reaction chamber, for example, to enable the sample to be moved into the reaction chamber.

In other embodiments, detection systems 600A and 600 and/or detection units 300, 201, and 200 as may have been described may be implemented in a diagnostic kit to be used in vitro for physician office lab, emergency room or other at patient bed applications. An in-vitro diagnostic kit may typically be contained in a housing shaped for table top or hand set including display system to provide display of data, control, and power that may be provided by an internal battery.

Other suitable operations or sets of operations may be used.

Figure 7:
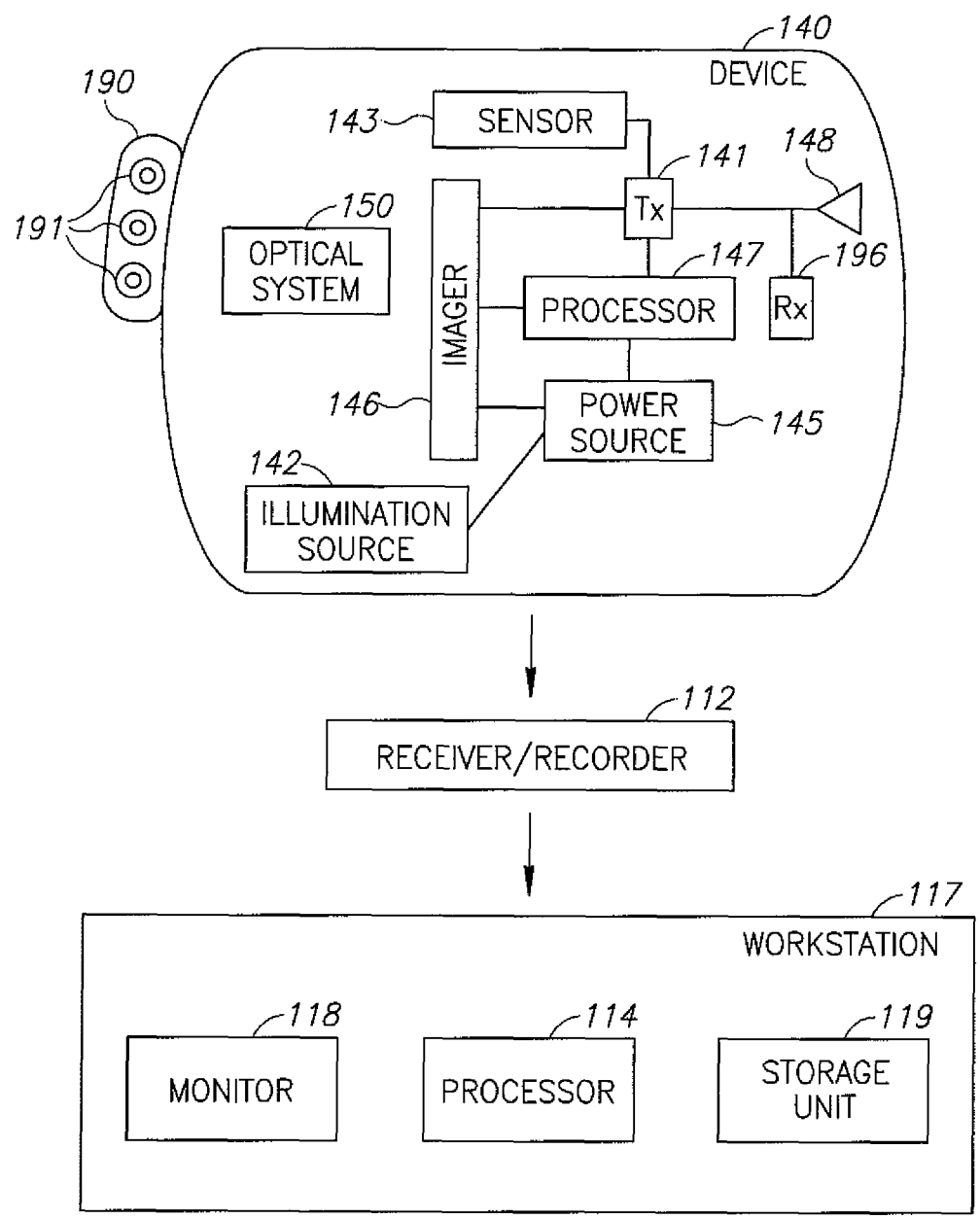
FIG. 7 is a schematic illustration of an in-vivo sensing system in accordance with some embodiments of the invention.

As shown in FIG. 7, in some embodiments, device 140 may include a carrier substance 190, e.g., a hydrogel, which may be immobilized or otherwise mounted or coated on an external portion of device 140, e.g., over a dome-shaped optical window of device 140. Carrier substance 190 may include, for example, conjugated liposomes or nano-containers 191.

In some embodiments, carrier substance 190 may be made of or may include crosslinked polymeric chains, in which water or water-based solutions may be dispersed or adsorbed, for example, a hydrogel e.g., a network of polymer chains that are water-soluble, or a colloidal gel in which water is the dispersion medium, or micelles or polymeric compounds, e.g., cellulose; other absorbent or super-absorbent natural or synthetic polymers may be used. In another embodiment, dried formulations may be used, e.g. lyophilize liposomes or polymerosomes may be embedded in nitrocellulose. In other embodiments, preservatives (e.g., Thimerosal, benzyl alcohol, parabens, or the like) may be used or added.

Figure 8:
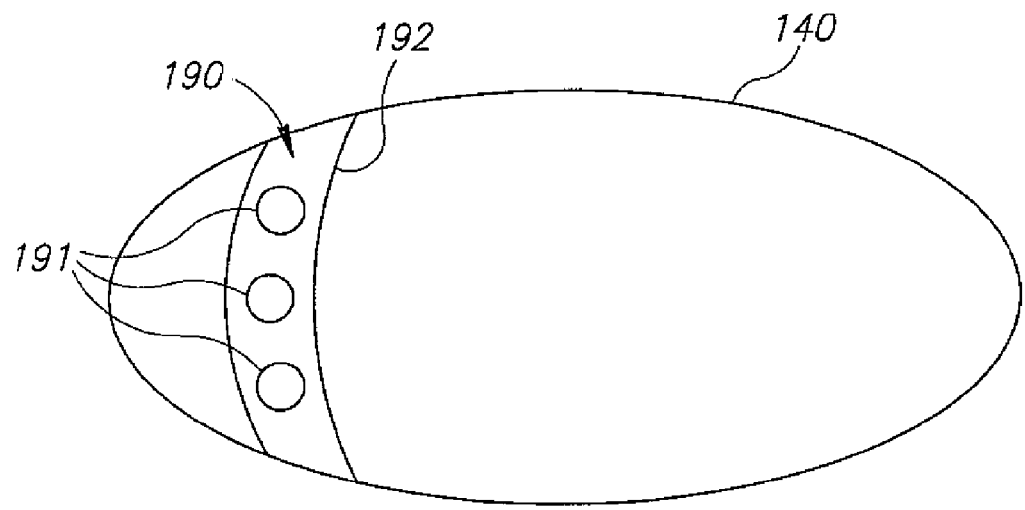
FIG. 8 is a schematic illustration of an in-vivo imaging device in accordance with an embodiment of the invention.

In some embodiments, for example, as illustrated in FIG. 8, carrier substance 190 and liposomes or nano-containers 191 may be placed in, or immobilized onto, a band 192, e.g., mounted or coated around or over a portion of device 140, or around or over a portion of a window or a suitable trench in the dome-shaped window of device 140

Figure 9:
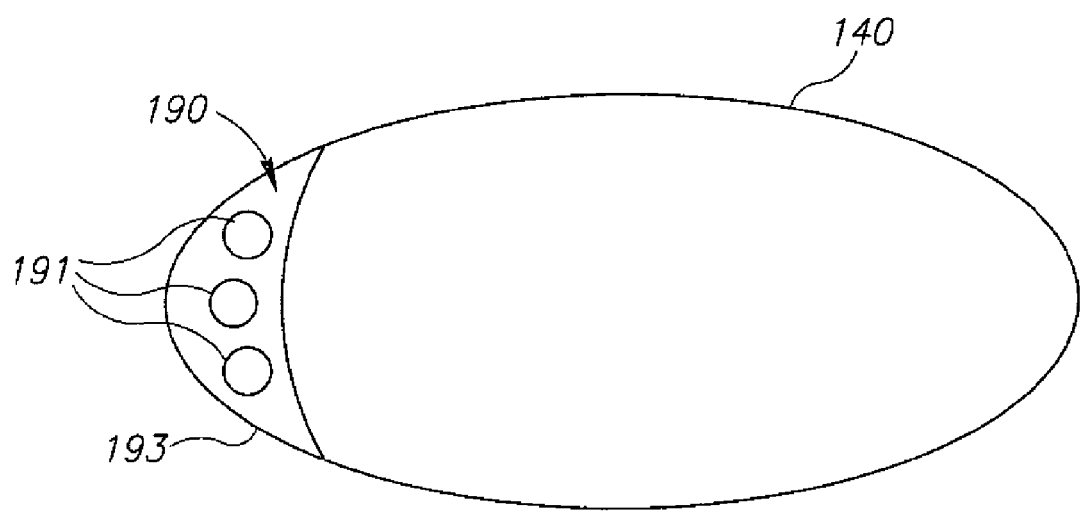
FIG. 9 is a schematic illustration of an in-vivo imaging device in accordance with another embodiment of the invention.

In some embodiments, for example, as illustrated in FIG. 9, earlier substance 190 and liposomes or nano-containers 191 may be placed in, or immobilized onto, an external dome-shaped portion 193, e.g., mounted or coated over a portion of device 140, or around or over a window or dome-shaped window of device 140

In some embodiments, the carrier substance 190 (e.g., hydrogel) may be coated, for example, for preservation and/or storage while the device 140 is not in-vivo. For example, the coating may dissolve in-vivo, or only when the device 140 reaches a certain body part (e.g., the colon). In some embodiments, the coating may partially dissolve, for example, to open an inlet gate and/or an outlet gate, thereby creating a flow (e.g., a contuse flow) through the carrier substance 190.

Although FIG. 8 and FIG. 9 demonstrate the placement of carrier substance 190 and liposomes or nano-containers 191 externally to the in-vivo device 140, other suitable locations may be used. In some embodiments, for example, carrier substance 190 and liposomes or nano-containers 191 may be placed internally to device 140, e.g., within an internal compartment or chamber or channel, which may be subsequently opened in-vivo (e.g., using a dissolvable gate, a mechanical gate, or the like). Other suitable placement, mounting or coating methods may be used.

For example, in some embodiments, a reaction chamber within the in-vivo device 140 or connected to the in-vivo device 140 may contain immobilized the liposomes or nano-containers 191 for carrying imaging agents that may be specifically reactant to a target analyte. Such liposomes or nano-containers 191 may include, for example, liposomes, colloidosomes and/or polymerosomes; other suitable nano-containers may be used. In some embodiments, for example, liposomes or nano-containers 191 may include bilayers of phospholipids around a hydrophobic core; in other embodiments, liposomes or nano-containers 191 may be composed of more than bilayers and may include a multilayer of confronting lipid layers.

In some embodiments, conjugated liposomes or nano-containers 191 (e.g., lyophilized conjugated liposomes, or a liposome having a conjugated antibody integrated therein) may be filled with, for example, pH sensitive color in low strength buffer possessing a pH different from and/or opposite that of the sample and/or analyte. Rupture of the liposomes or nano-containers 191 may occur as a result of a reaction with a target analyte. Upon rupturing of the liposomes or nano-containers 191 and exposure of, for example, the pH sensitive color to the sample, a change of color may occur that may be, for example, optically detectable and/or visible and/or may be imaged. In other embodiments, liposomes or nano-containers 191, e.g., polymersome, may include or may be filled with an alternate or additional molecule (e.g., fluorescence material, material having fluorescence properties, or the like) capable of changing optical properties of a substrate.

Figure 10A:
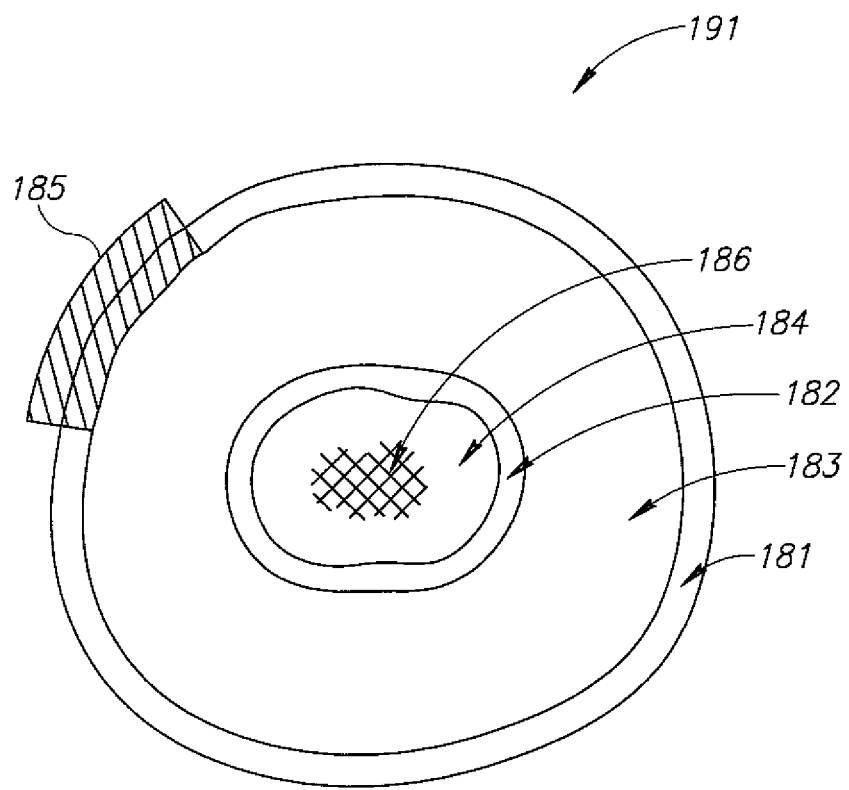
FIG. 10A is a schematic illustration of a liposome or nano-container in accordance with some embodiments of the invention.
Figure 10B:
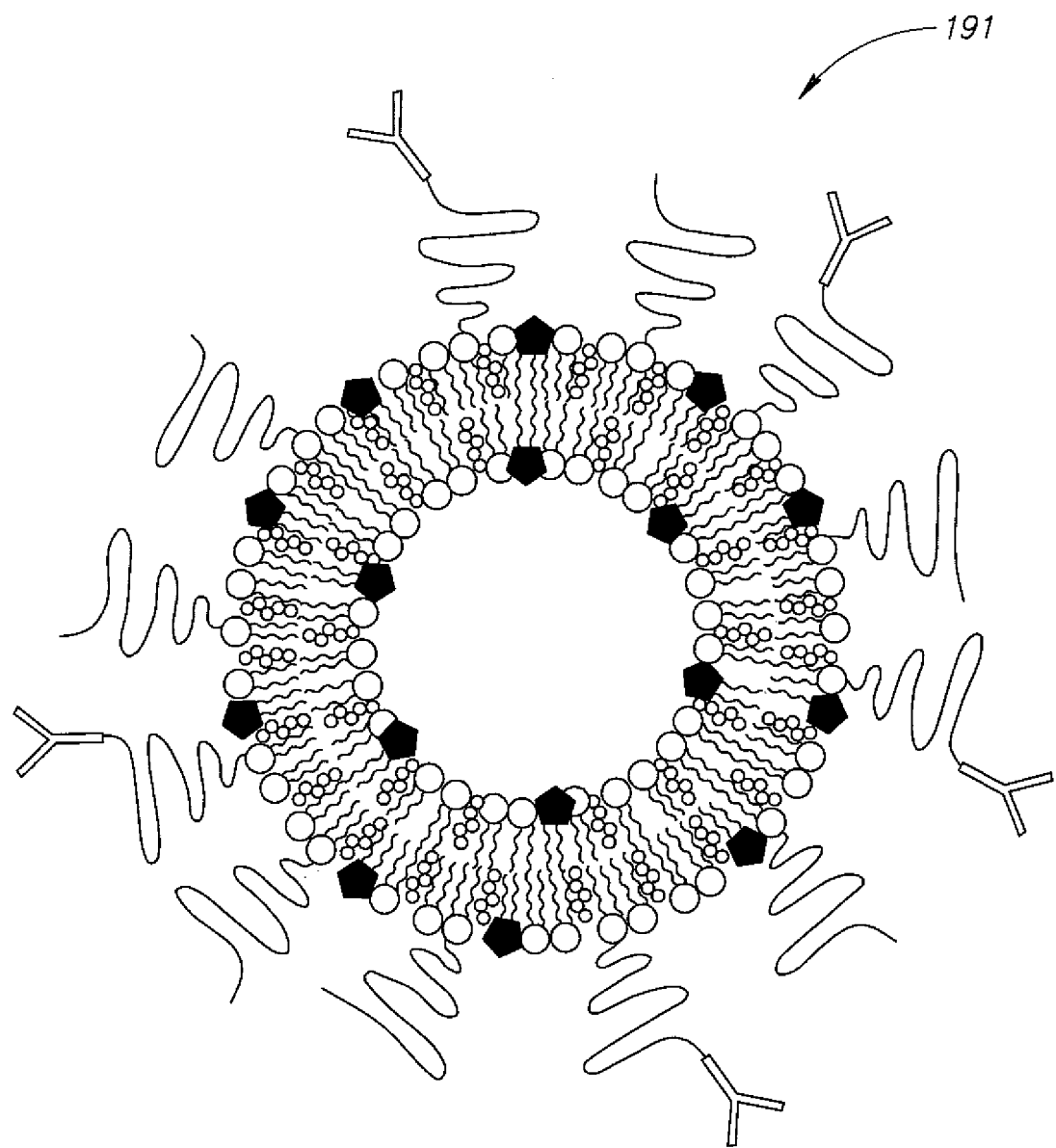
FIG. 10B is an illustration of a liposome or nano-container in accordance with some embodiments of the invention.

Reference is made to FIG. 10A, which illustrates a liposome or nano-container 191 in accordance with some embodiments of the invention, and to FIG. 10B, which illustrates a liposome or nano-container 191 in accordance with some embodiments of the invention. Liposome or nano-container 191 may be or may include, for example, a microscopic self-assembling spherical vesicle (e.g., liposome, nanosome, or the like) having a membrane composed of, e.g., a phospholipid bilayer. Liposome or nano-container 191 may include, for example, organic materials, inorganic materials, synthetic materials or polymers, polyphosphate-based materials, or the like. Liposome or nano-container 191 may be a fluid-filled pouch or compartment, whose walls are made of layers of phospholipids which may be substantially identical to the phospholipids of cell membranes. Liposome or nano-container 191 may have a diameter of approximately 50 nanometers, approximately 100 nanometers, or the like.

In some embodiments, for example, a first shell 181, e.g., an external shell, of the liposome or nano-container 191 may be water insoluble; whereas a second shell 182, e.g., an internal shell, of the liposome or nano-container 191 may be water soluble. In some embodiments, for example, a zone between the first shell 181 and the second shell may be used as a first nano-compartment 183, e.g., a hydrophobic cavity; whereas a zone inside the second shell 182 may be used as a second nano-compartment 184, e.g., a polar cavity. Other numbers or locations of layers, shells, zones and/or nano-compartments may be used.

In some embodiments, an external layer (or a portion of an external layer) of the liposome or nano-container 191 may include, or may be connected to, a reactant or reagent 185. For example, the reactant or reagent 185 may be or may include a protein, a hormone, an enzyme, an antibody, a targeting agent, an active part of an antibody, a "hotspot" of an antibody or a protein (e.g., minimal functional domains involved in protein-to-protein interactions and sufficient to induce a biological or chemical response), a modified antibody, a modified antigen, or the like. For example, reactant or reagent 185 may include a specific protein or antibody which may react when in contact with a certain antigen or pathology, e.g., a tumor, a cancerous tumor, an infection, a polyp, or the like. In some embodiments, for example, reactant or reagent 185 may include, for example, pepsin, pepsin 1, pepsin 3, gastrin, gastrin 17, or various other reactants or reagents.

In some embodiments, liposome or nano-container 191 may store therein (e.g., within nano-compartment 183 and/or 184) a signaling material 186. The signaling material 186 may be or may include, for example, a pH-sensitive substance or indicator, a fluorescent substance or indicator, or another substance or indicator which may modify its optical properties (e.g., its color or its light emission or absorption properties) upon modification of the signaling material 186 or upon reaction between the signaling material 186 and another substance (e.g., targeted protein or an analyte present in body fluid). For example, in some embodiments, signaling material 186 may initially (e.g., when stored within liposome or nano-container 191) have a first color, e.g., blue; and may modify its color to a second, different color, e.g., yellow, if signaling material 186 reacts with a body substance or with another material substance present in hydrogel 190.

In some embodiments, for example, signaling material 186 may have a first color or a first fluorescence or a first optical property in the presence of a first substance, and a second color or a second fluorescence or a second optical property in the presence of a second substance. In some embodiments, for example, signaling material 186 may have a first color or a first fluorescence. Or a first optical property in the presence of a first pH level or a first acidity level, and a second color or a second fluorescence or a second optical property in the presence of a second pH level or a second acidity level. In some embodiments, for example, signaling material 186 may have a first color or a first fluorescence or a first optical property in the presence of a water-based substance, and a second color or a second fluorescence or a second optical property in the presence of a lipid-based substance.

Referring again to FIG. 7, the device 140 may be inserted in-vivo, for example, by swallowing a swallowable capsule, and may pass through a body lumen. The liposome or nano-container 191 may be in contact with a body substance which may react with reactant or reagent 185, e.g., a certain antigen or pathology, a tumor, a cancerous tumor, an infection, a polyp, or the like. The reaction may cause breaking, opening, rupture, collapsing, dissolution, fusion, or puncturing of liposome or nano-container 191, or of one or more layers (e.g., an external layer, or a portion thereof) of liposome or nano-container 191. For example, one or more holes, outlets, punctures or openings may be created, allowing the signaling material 186 stored within liposome or nano-container 191 to exit and/or to be in contact with the body substance or with the carrier substance 190 (e.g., the hydrogel); thereby resulting in a modification of an optical property of signaling material 186 (e.g., color or fluorescence; for example, modification from blue color to yellow color, or the like).

In some embodiments, for example, signaling material 186 may include or may be bromothymol blue (indicator) in a solution with low buffer capacity at a pH of approximately 8 or above having a blue color. When liposome or nano-container 191 is in contact with healthy stomach acid, the acid may not penetrate the liposome or nano-container 191, there may be no contact between the acid and the signaling material 186 (e.g., the indicator), and thus liposome or nano-container 191 may remain blue. In contrast, if the stomach acid contains targeted proteins, e.g., above a threshold value, liposome or nano-container 191 may deteriorate, the stomach acid may be in contact with the signaling material 186 (e.g., the indicator), and the signaling material 186 (e.g., the indicator) may modify its color (or other optical property), e.g., from blue to yellow.

In some embodiments, the modification of optical property of the signaling material 186, or the resulting optical property of signaling material 186, may be imaged or otherwise sensed, e.g., by imager 146 of in-vivo device 140. For example, imager 146 may acquire one or more images, e.g., through a window or a dome-shaped window of device 140. The acquired image may include, for example, the signaling material 186 having a modified (e.g., non-original) color, and/or a body lumen in which the reaction takes place. The detection of the modification of the optical property of signaling material 186, and/or the detection of signaling material 186 which may now be external to the liposome or nano-container 191, may indicate that a reactance took place between reagent or reactant 185 and its corresponding antigen, and may indicate the presence of the corresponding antigen, e.g., a pathology, a tumor, a cancerous tumor, an infection, a polyp, or the like.

In some embodiments, for example, the liposome or nano-container 191 may be initially filled with pH-sensitive substance having a first color (e.g., blue). The liposome or nano-container 191 may rupture as a result of reaction with a target, e.g., a certain antigen. The pH-sensitive substance stored within the liposome or nano-container 191 may modify its color into a second color (e.g., yellow). The in-vivo imager 146 may acquire images of the modified color, and the image data may be transmitted by transmitter 141.

In some embodiments, device 140 may transmit digital color image information which may include color information of the liposome or nano-container 191, e.g., in discrete portions; for example, a discrete portion may correspond to an image or a flame; other suitable transmission methods may be used. In some embodiments, device 140 may capture and/or acquire an image, for example, once every half second; other capture rates, constant or variable, may be used. In some embodiments, device 140 may be used for locating the disorder or pathology, and/or for determining its nature, e.g., distinguishing between a benign and malignant polyps or tumors.

In other embodiments, for example, the liposome or nano-container 191 may be initially filled with fluorescent substance. The liposome or nano-container 191 may rupture as a result of reaction with a target, e.g., a certain antigen. The fluorescent substance stored within the liposome or nano-container 191 may be exposed or may exit the liposome or nano-container 191 and as a result change (e.g., increase) its excitation properties. The in-vivo imager 146 or the sensor 143 (e.g., a light sensor) may acquire the images and/or the change (e.g., increase) in signal of the fluorescent substance, and the sensed data may be transmitted by transmitter 141, e.g., in addition to or instead of the relevant image data.

In some embodiments, in-vivo device 140 may be localized, e.g., using one or more localization methods, thereby allowing to determine the location or body part in which the reaction took place, e.g., the location or body part having the antigen, pathology, tumor, cancerous tumor, infection, polyp, or the like.

Figure 11:
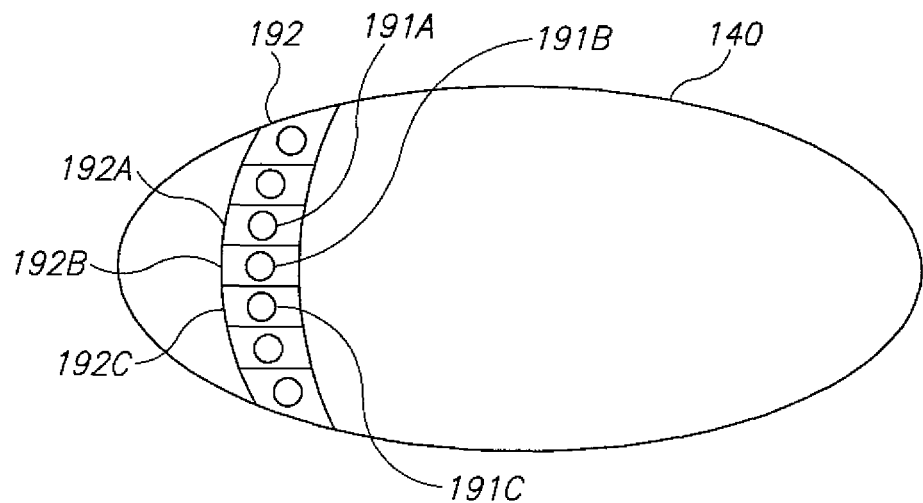
FIG. 11 is a schematic illustration of an in-vivo imaging device in accordance with yet another embodiment of the invention.

FIG. 11 illustrates an in-vivo device 140 having multiple types of liposomes or nano-containers 191, in accordance with some embodiments of the invention. For example, carrier substance 190 and liposomes or nano-containers 191 may be placed in, or immobilized onto, a band 192, e.g., mounted or coated around or over a portion of device 140, or around or over a portion of a window or dome-shaped window of device 140. Band 192 may include multiple portions or areas, for example, a first portion 192A, a second portion 192B, a third portion 192C, or the like; and each portion may include, for example, a different type of liposomes or nano-containers, e.g., a first type of liposomes or nano-containers 191A, a second type of liposomes or nano-containers 191B, a third type of liposomes or nano-containers 191C, respectively. For example, the first type of liposomes or nano-containers 191A may be adapted to react to a first antigen or protein, the second type of liposomes or nano-containers 191A may be adapted to react to an enzyme or protein, the third type of liposomes or nano-containers 191A may be adapted to react to a tertian hormone or protein, or the like.

In-vivo device 140 of FIG. 5 may pass through a body lumen, e.g., the GI tract. The first type of liposomes or nano-containers 191A may be in contact with the first antigen or protein, thereby causing rupture of the liposome or nano-container 191A, and modification of optical property of the content of liposome or nano-container 191A. Similarly, third type of liposomes or nano-containers 191C may be in contact with the hormone or third protein, thereby causing rupture of the liposome or nano-container 191C, and modification of optical property of the content of liposome or nano-container 191C. In contrast, the second type of liposomes or nano-containers 191B may not be in contact with the enzyme or second protein (e.g., if the enzyme is not present in the patient's body or GI tract), and the content of the second type of liposome or nano-container 191B may not be exposed or may not modify its optical property. Device 140 may acquire images including the first portion 192A, the second portion 192B, and the third portion 192C. The in-vivo images may indicate, for example, that the first and third antigens are detected and may be present in-vivo, whereas the second antigen are not detected and possible may not be present in-vivo.

In some embodiments, reaction by the first type of liposomes or nano-containers 191A may result in a first modification of optical property (e.g., change of color from blue to yellow), whereas reaction by the by the second type of liposomes or nano-containers 191B may result in a second, different, modification of optical property (e.g., change of color from blue to green, or exposure of fluorescent substance).

In some embodiments, reaction by a first type of liposomes or nano-containers 191A may result in a first modification of optical property (e.g., change of color from blue to yellow); whereas reaction by the by a second type of liposomes or nano-containers 19B may result in a second, different, modification of non-optical properties, e.g., modification in magnetic field or conductivity, which may be detected by sensor 143.

In other embodiments, multiple reactions may result in similar, or even substantially identical, modifications of optical property, and may be differentiated or distinguished, for example, based on the location or the relative location of the portions. For example, a change of color from blue to yellow in the first portion 192A, may be distinguished from a change of color from blue to yellow in the third portion 192C, based on the location or the relative location of portions 192A and 192C on the band 192 as imaged by the in-vivo device 140. For example, a change of color from a first color to a second color at the location of the first portion 192A, may be used as indication that the first type of liposomes or nano-containers 191A reacted with a first type of antigen; whereas a change of color from the first color to the second color at the location of the first portion 192C, may be used as indication that the third type of liposomes or nano-containers 191C reacted with a third type of antigen.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An in vivo device to detect the presence of an analyte in a fluid sample comprising:
   an inlet for obtaining the fluid sample in vivo;
   a reaction chamber in which nanocontainers are immobilized, said nanocontainers carrying imaging agents that are reactant to a target analyte in the fluid sample; and
   an imager on board said in vivo device for imaging the reaction chamber.

2. The in vivo device according to claim 1 wherein said nanocontainers are liposomes.

3. The in vivo device according to claim 2, wherein said liposomes comprise bilayers of phospholipids around a hydrophobic core.

4. The in vivo device according to claim 2, wherein said liposomes comprise a multilayer of confronting lipid layers around a hydrophobic core.

5. The in vivo device according to claim 1, wherein said imaging agents are a signaling material.

6. The in vivo device according to claim 5, wherein said signaling material is a pH sensitive color in low strength buffer possessing a pH different from that of the sample and/or analyte.

7. The in vivo device according to claim 5, wherein said signaling material is a fluorescent material capable of changing optical properties of the target analyte.

8. The in vivo device according to claim 5, wherein said signaling material has a first color, which is modified to a second, different color when said signaling material reacts with a target analyte in the fluid sample.

9. The in vivo device according to claim 1, wherein said device further comprises a storage chamber including a dry buffer, and a gate to fluidically connect the storage chamber to the reaction chamber.

10. The in vivo device according to claim 1, wherein said device comprises a plurality of storage chambers, reaction chambers, and waste chambers to simultaneously test for different analytes in a sample.

11. The in vivo device according to claim 1, wherein said device further comprises a storage chamber comprising an antibody-antigen-congregate at a predetermined concentration to serve as a reference to the reaction chamber.

12. The in vivo device according to claim 1, wherein at least part of the reaction chamber is transparent and is in an optical path of the imager.

13. The in vivo device according to claim 1 wherein the in vivo device is an autonomous ingestible capsule.

14. The in-vivo device according to claim 1, wherein said device further comprises a waste chamber and a gate to fluidically connect the reaction chamber to the waste chamber.

15. The in vivo device according to claim 14, wherein a pressure gradient between the waste chamber and the reaction chamber facilitates flow when the gate is opened.

16. A method for detecting the presence of an analyte in an in vivo fluid sample, the method comprising:
   collecting the in vivo fluid sample into a detection system in vivo, wherein the detection system comprises:
      an inlet for obtaining the fluid sample in vivo;
      a reaction chamber in which nanocontainers are immobilized, said nanocontainers carrying imaging agents that are reactant to a target analyte in the fluid sample; and
   detecting a reaction between an analyte in the fluid sample and the nanocontainer; and
   imaging the reaction chamber.

17. The method according to claim 16 wherein said nanocontainers are liposomes.

18. The method according to claim 16, wherein said reaction between an analyte in the fluid sample and the nanocontainer results in rupture of the nanocontainer, which exposes the imaging agents to be optically detectable and/or visible.

19. A system to detect the presence of an analyte in a fluid sample comprising:
   an in vivo device comprising:
      an inlet for obtaining the fluid sample in vivo;
      a reaction chamber in which nanocontainers are immobilized, said nanocontainers carrying imaging agents that are reactant to a target analyte in the fluid sample;
      an imager for imaging in vivo and a portion of the reaction chamber: and
      a transmitter for transmitting image data;
   an external receiver device;
   an external processor with a display unit; wherein the external processor is configured to display images obtained by the imager.

20. The system according to claim 19, wherein the fluid sample is of the GI tract.

21. The in vivo device according to claim 19, wherein said nanocontainers are liposomes.

22. The system according to claim 19, wherein said device further comprises a waste chamber and a gate to fluidically connect the reaction chamber to the waste chamber.

* * * * *